(12) United States Patent
Seubert et al.

(10) Patent No.: US 7,427,392 B1
(45) Date of Patent: Sep. 23, 2008

(54) METHODS FOR AIDING IN THE DIAGNOSIS OF ALZHEIMER'S DISEASE BY MEASURING AMYLOID-β PEPTIDE (X-≧41) AND TAU

(75) Inventors: Peter A. Seubert, South San Francisco, CA (US); Carmen Vigo-Pelfrey, Mountain View, CA (US); Dale B. Schenk, Pacifica, CA (US); Robin Barbour, Newark, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 08/466,554

(22) Filed: Jun. 6, 1995

Related U.S. Application Data (60) Division of application No. 08/419,008, filed on Apr. 7, 1995, now abandoned, which is a continuation-in-part of application No. 08/339,141, filed on Nov. 14, 1994.

(51) Int. Cl.
*A61K 49/00* (2006.01)
(52) U.S. Cl. .......................................... 424/9.2; 800/3
(58) Field of Classification Search .................... 435/4, 435/6, 7.1, 7.21, 7.92, 172.3; 536/23.1, 23.5; 800/2, 3; 424/9.1, 9.2
See application file for complete search history.

(56) References Cited

U.S. PATENT DOCUMENTS

| | | | |
|---|---|---|---|
| 4,271,140 A | | 6/1981 | Bunting |
| 4,474,892 A | | 10/1984 | Murad et al. |
| 4,666,829 A | | 5/1987 | Glenner et al. .................. 435/6 |
| 5,387,742 A | * | 2/1995 | Cordell .......................... 800/2 |
| 5,547,841 A | * | 8/1996 | Marotta et al. |
| 5,593,846 A | | 1/1997 | Schenk et al. |
| 5,604,102 A | * | 2/1997 | McConlogue et al. |
| 5,612,486 A | * | 3/1997 | McConlogue et al. |
| 5,750,349 A | | 5/1998 | Suzuki et al. |
| 5,766,846 A | | 6/1998 | Schlossmacher et al. |
| 5,837,672 A | | 11/1998 | Schenk et al. |
| 6,114,133 A | | 9/2000 | Seubert et al. |
| 6,284,221 B1 | | 9/2001 | Schenk et al. |
| 6,610,493 B1 | | 8/2003 | Citron et al. |
| 2003/0148392 A1 | | 8/2003 | Citron et al. |
| 2004/0253643 A1 | | 12/2004 | Seubert et al. |
| 2004/0265920 A1 | | 12/2004 | Seubert et al. |
| 2005/0069968 A1 | | 3/2005 | Seubert et al. |

FOREIGN PATENT DOCUMENTS

| | | |
|---|---|---|
| AU | 705907 | 9/1999 |
| CA | 2205359 | 7/2006 |
| EP | 0 444 856 A2 | 9/1991 |
| EP | 0 683 234 A1 | 11/1995 |
| EP | 0-683-234 A1 | 11/1995 |
| EP | 0 667 959 | 8/2003 |
| EP | 0 792 458 | 10/2004 |
| WO | WO 90/12870 | 11/1990 |
| WO | WO 90/12871 | 11/1990 |
| WO | WO 93/14200 | 7/1993 |
| WO | WO 94/10569 A1 | 5/1994 |
| WO | WO 96/15452 A1 | 5/1996 |
| WO | WO 96/25435 | 8/1996 |
| WO | WO 97/048983 A1 | 12/1997 |
| WO | WO 01/62284 A2 | 8/2001 |

OTHER PUBLICATIONS

Games etal, Nature, 373:523-527, Feb. 9, 1995.*
Vigo-Pelfrey, Journal of Neurochemistry, 61:1965-1968, 1993.*
Iwatsubo et al, Neuron, 13:45-53, Jul. 1994.*
Seubert et al, Nature., 359:325-327, Sep. 24, 1992.*
Aukuchi etal, Annals of the New York Academy of Sciences, 695:217-223, 1993.*
Uno et al, Annals of the New York Academy of Sciences, 695:232-235, 1993.*
Lannfelt etal, Behavorial Brain Research, 57:203-213, 1993.*
Suzuki etal, Science, 164:1337-1340, May 27, 1994.*
Fukuchi et al Annals of the New York Academy of Sciences, 1992 pp. 217-223.*
Felenstein etal. in Alzheimer's and Parkinson's Diseases, I. Hanin ed. Plenum Press, Ny, p. 406 col. 1, 1995.*
Lanfelt etal, Behav. Brain. Res. 57, all pages, 1993.*
C. Vigo-Pelfrey et al. (1994) *Society for Neuroscience Abstracts* vol. 20 #191.2 Detection of Aβ$_{1-42}$ In CSF And Various Cell Conditioned Media.
K. Urakami et al. (1992) *Acta Neurol Scand* 85:343-346. Amyloid βprotein precursors with kunitz-type inhibitor domains and acetyl-cholinesterase in cerebrospinal fluid from patients with demential of the Alzheimer type.
R. Prior et al. (1991) *Neuroscience Letters* 124:69-73. Quantitative changes in the amyloid βA4 precursor protein in Alzheimer cerebrospinal fluid.
B. McDonald et al. (1988) *Alzheimer Disease and Associated Disorders* 2(3):186. The Characterisation And Purification Of A Protein Present In Cerebrospinal Fluid And Serum, Using A Monoclonal Antibody Which Reacts Immunohistochemically With Amyloid Deposits In Alzheimer Brains.
D. Allsop (1986) *Neuroscience Letters* 68:252-256. Monoclonal Antibodies Raised Against A Subsequence Of Senile Plaque Core Protein React With Plaque Cores, Plaque Periphery And Cerebrovascular Amyloid In Alzheimer's Disease.

(Continued)

*Primary Examiner*—Patricia A. Duffy
(74) *Attorney, Agent, or Firm*—Townsend and Townsend and Crew LLP (57) ABSTRACT

This invention provides methods useful in aiding in the diagnosis of Alzheimer's disease. The methods involve measuring the amount of amyloid-β peptide (x-≧41) in the cerebrospinal fluid of a patient. High levels of the peptide generally are inconsistent with a diagnosis of Alzheimer's. Low levels of the peptide are consistent with the disease and, with other tests, can provide a positive diagnosis. Other methods involve measuring the amounts of both Aβ(x-≧41) and tau. Low levels of Aβ(x-≧41) and high levels of tau are a positive indicator of Alzheimer's disease, while high levels of Aβ(x-≧41) and low levels of tau are a negative indication of Alzheimer's disease.

8 Claims, 4 Drawing Sheets

OTHER PUBLICATIONS

T. Ishii (1986) *Neuropathology and Applied Neurobiology* 12:441-445. A Monoclonal Antibody To Amyloid In The Brains Of Patients With Alzheimer's Disease.
Haass et al. (1992) *Nature* 359:322-325. Amyloid β-peptide is produced by cultured cells during normal metabolism.
Wolozin et al. (1987) *Annals of Neurology* 22(4):521-526. Alzheimer-Related Neuronal Protein A68: Specificity and Distribution.
Ueda et al. (1990) *The Journal of Neuroscience* 10(10):3295-3304. Alz-50 Recognizes a Phosphorylated Epitope of Tau Protein.
Chui et al. (1993) *Arch Neurol* 50:57-63. Reliability and Usefulness of a New Immunochemical Assay for Alzheimer's Disease.
van Gool and Bolhuis, "Cerebrospinal Fluid Markers of Alzheimer's Disease", *JAGS*, 39:1025-1039 (1991).
Scheuner, D. et al., "Secreted amyloid beta-protein similar to that in the senile plaques of Alzheimer's disease is increased in vivo by the presenilin 1 and 2 and APP mutations linked to familial Alzheimer's disease." Nature Medicine, Aug. 1996, vol. 2, No. 8, pp. 864-870.
Spitzer, Chair, Work Group to Revise DSM-III, Diagnostic and Statistical Manual of Mental Disorders (Third Edition-Revised), 1987, 119-121 American Psychiatric Association, Washington, D.C.
Glenner and Wong (1984) Biochem. Biophys. Res. Commun. 120:885-890. Alzheimer's Disease: Inital Report Of The Purification And Characterization Of A Novel Cerebrovascular Amyloid Protein.
Kang et al. (1987) Nature 325:733-736. The precursor of Alzheimer's disease amyloid A4 protein resembles a cell-surface receptor.
Roher et al. (1993) Proc. Natl. Acad. Sci. USA 90:1086-840. β-Amyloid-(1-42) is a major component of cerebrovascular amyloid deposits: Implications for the pathology of Alzheimer disease.
Iwatsubo et al. (1994) Neuron 13:45-53. Visualization of Aβ42 (43) and Aβ40 in Senile Plaques with End-Specific Aβ Monoclonals: Evidence That an Initially Deposited Species Is Aβ42 (43).
Selkoe (1994) J. Neuropath. and Exp. Neurol. 53:438-447. Alzheimer's Disease: A Central Role for Amlyoid.
Selkoe (1991) Neuron 6:487. The Molecular Pathology of Alzheimer's Disease.
Goate et al. (1991) Nature 349:704-706. Segration of a missense mutation in the amlyoid precursor protein gene with familial Alzheimer's disease.
Chartier Harlan et al. (1991) Nature 353:844-846. Early-onset Alzheimer's disease caused by mutations at codon 717 of the β-amyloid precursor protein gene.
Murrell et al. (1991) Science 254:97-99. A Mutation in the Amyloid Precursor Protein Associated with Hereditary Alzheimer's Disease.
Suzuki et al. (1994) Science 264:1336-1340. An Increased Percentage of Long Amyloid β Protein Secreted by Familial Amyloid β Protein Precursor (βAPP$_{717}$) Mutants.
Mullan et al. (1992) Nature Genet 1:345-347. A pathogenic mutation for probable Alzheimer's disease in the APP gene at the N-terminus of β-amyloid.
Glenner and Wong (1984) Biochem. Biophys. Res. Commun. 122:1131-1135. Alzheimer's Disease And Down's Syndrome: Sharing Of A Unique Cerebrovascular Amyloid Fibril Protein.
Masters et al. (1985) Proc. Natl. Acad. Sci USA 82:4245-4249. Amyloid plaque core protein in Alzheimer disease and Down syndrome.
Selkoe et al. (1986) J. Neurochem. 46:1820-1834. Isolation of Low-Molecular-Weight Proteins from Amyloid Plaque Fibers in Alzheimer' Diease.
Joachim et al. (1988) Brain Research 474:100-111. Protein chemical and immunocytochemical studies of meningovascular β-amyloid protein in Alzheimer's disease and normal aging.
Hilbich et al. (1991) J. Mol. Biol. 218:149-163. Aggregation and Secondary Structure of Synthetic Amyloid βA4 Peptides of Alzheimer's Disease.
Barrow and Zagorski (1991) Science 253:179-182. Solution Structures of β Peptide and Its Constituent Fragments: Relation to Amyloid Deposition.
Burdick et al. (1992) J. Biol. Chem. 267:546-554. Assembly and Aggregation Properties of Synthetic Alzheimer's A4/β Amyloid Peptide Analogs.

Palmert et al. (1989) Proc. Natl. Acad. Sci. USA 86:6338-6342. The β-amyloid protein precursor of Alzheimer disease has soluble derivatives found in human brain and cerebrospinal fluid.
Weidemann et al. (1989) Cell 57:115-126. Identification, Biogenesis, and Localization of Precursors of Alzheimer's Disease A4 Amyloid Protein.
Henriksson et al. (1991) J. Neurochem. 56:1037-1042. Analysis and Quantitation of the β-Amyloid Precursor Protein in the Cerebrospinal Fluid of Alzheimer's Disease Patients with a Monolconal Antibody-Based Immunoassay.
Palmert et al. (1990) Neurology 40:1028-1034. Soluble derivatives of the β amyloid protein precuror in cerebrospinal fluid: Alterations in normal aging and in Alzheimer's disease.
Seubert et al. (1993) Nature 361:260-263. Secretion of β-amyloid precursor protein cleaved at the amino terminus of the β-amyloid peptide.
Podlisny et al. (1990) Biochem. Biophys. Res. Commun. 167:1094-1101 Detection Of Soluble Forms Of The β-Amyloid Precursor Protein In Human Plasma.
Rumble et al. (1989) N. Engl. J. Med. 320:1446-1452. Amyloid A4 Protein And Its Precursor In Down's Syndrome And Alzheimer's Disease.
Schlossmacher et al. (1992) Neurobiol. Aging 13:421-434. Detection of Distinct Isoform Patterns of the β-Amyloid Precursor Protein in Human Platelets and Lymphocytes.
Wong et al. (1984) Proc. Natl. Acad. Sci USA 82:8729-8732. Neuritic plaques and cerebrovascular amyloid in Alzheimer disease are antigenically related.
Selkoe (1986) Neurobiol. Aging 7:425-432. Altered Structural Proteins in Plaques and Tangles: What do They Tell Us About the Biology of Alzheimer's Disease?.
Pardridge et al. (1987) Biochem. Biophys. Res. Commun. 145:241-248. High Molecular Weight Alzheimer's Disease Amyloid Peptide Immunoreactivity In Human Serum And CSF Is An Immunoglobulin G.
Joachim et al. (1989) Nature 341:226-230. Amyloid β-protein deposition in tissues other than brain in Alzheimer's disease.
Selkoe et al. (1989) Neurobiol. Aging 10:387-395. Molecular Pathology of Amyloidogenic Proteins and the Role of Vascular Amyloidosis in Alzheimer's Disease.
Wisniewski, Alzheimer's disease, eds. Becker and Giocobini, Taylor and Francas, N.Y. p. 206, 1990. Alzheimer Disease, A Current Research in Early Diagnosis.
Kim and Wisniewski, Techniques in Diagnostic Pathology, eds, Bullock et al., Academic Press, Boston p. 106. Techiniques in Diagnostic Pathology.
Seubert et al. (1992) Nature 359:325-327. Isolation and quantification of soluble Alzheimer's β-peptide from biological fluids.
Vigo-Pelfrey et al. (1993) J. Neurochem. 61:1965-1968. Characterization of β-Amyloid Peptide from Human Cerebrospinal Fluid.
Esch et al. (1990) Science 248:1122 Cleavage of Amyloid β Peptide During Constitutive Processing of Its Precursor.
Anderson et al. (1991) Neuro Science Lett. 128:126-128. Exact cleavage site of Alzheimer anyloid precursor in neuronal PC-12 Cells.
Ponte et al. (1988) Nature 331:525-527. A new A4 amyloid mRNA contains a domain homologous to serine proteinase inhibitors.
Tanzi et al. (1988) Nature 331:528-530. Protease inhibitor domain encoded by an amyloid protein precursor mRNA associated with Alzheimer's disease.
Kitaguchi et al. (1988) Nature 331:530-532. Novel precursor of Alzheimer's disease amyloid protein shows protease inhibitory activity.
Hardy (1992) Nature Genet. 1:233-234. Framing β-amyloid.
Z.S. Khachaturian (1985) Arch. Neurol. 42:1097-1105. Diagnosis of Alzheimer's Disease.
Vandermeeren et al. (1993) J. Neurochem. 61:1828-1834. detection of τ Proteins in Normal and Alzheimer's Disease Cerebrospinal Fluid with a Sensitive Sandwich Enzyme-Linked Immunosorbent Assay.
Mann et al. (1992) Neurodegeneration 1:201-295. The time course of pathological events in Down's Syndrome with particular reference to the involvement of microglial cells and deposits of β/A4.

Price et al. (1991) Neurob. Aging 12:295-312. The Distribution of Tangles, Plaques and Related Immunohistochemical Markers in Healthy Aging and Alzheimer'Disease.

Khatoon et al. (1992) J. Neurochem 59:750-753. Brain Levels of Microtubule-Associated Protein τ Are Elevated in Alzheimer's Disease: A Radioimmuno-Slot-Blot Assay for Nanograms of the Protein.

Goedert et al. (1989) Neuron 3:519-526. Multiple Isoforms of Human Microtubule-Associated Protein Tau: Sequences and Localization in Neurofibrillary Tangles of Alzheimer's Disease.

M. Goedert (1993) TINS 16:460-465. Tau protein and the neurofibrillary pathology of Alzheimer's disease.

Knops et al. (1991) J. Cell Biol. 114:725-733. Overexperssion of Tau in a Nonneuronal Cell Induces Long Cellular Processes.

Hachiniski et al. (1975) Arch. Neurol. 32:632-637. Cerebral Blood Flow in Dementia.

McKhann et al. (1984) Neurology 34:939-944. Clinical diagnosis of Alzheimer's disease: Report of the NINCDS-ADRDA Work Group under the auspices of Dept. of Health and Human Services Task Force on Alzheimer's Disease.

The Lund and Manchester Groups (1994) J Neurol Neurosurg Psychiatr 57:416-418. Clinical and neuropathological criteria for frontotemporal dementia.

E.S. Kawasaki in PCR Protocols: A guide to methods and applications. Academic Press, Inc., NY (1990) pp. 146-152. Sample Preparation From Blood, Cells, And Other Fluids.

Wenham et al. (1991) Lancet 337:1158-1159. Apolipoprotein E. Genotyping by one-stage PCR.

EPO Search Report for Application No. EP 04 077 711 (Feb. 17, 2005).

U.S. Appl. No. 09/649,891, filed Aug. 28, 2000, Schenk et al.

U.S. Appl. No. 08/466,554, filed Jun. 6, 1995, Seubert et al.

U.S. Appl. No. 08/419,008, filed Apr. 7, 1995, Seubert et al.

U.S. Appl. No. 07/965,972, filed Dec. 26, 1992, Schenk et al.

U.S. Appl. No. 07/911,647, filed Jul. 10, 1992, Schenk et al.

U.S. Appl. No. 60/186,295, filed Mar. 1, 2000, Chain.

Andreasen et al., "β-Amyloid (Aβ) protein in cerebrospinal fluid as a biomarker fro Alzheimer's disease," *Peptides*, 23:1205-1214 (2002).

Cai et al., :"Release of Excess Amyloid β Protein From a Mutant Amyloid β Protein Precursor," *Science*, 259:514-516 (1993).

Conference Program for the 24th Annual Meeting of the Society of Neurosciences, Nov. 13-18, 1994.

European Search Report for Application No. EP 95939892.6 dated Jan. 11, 1999.

Growdon et al., "Cerebrospinal Fluid Levels of Amyloid β-Protein are Independent of Apolipoprotein E Genotype and are Inversely Correlated With Severity of Dementia in Alzheimer's Disease," Soc. Neurosci. Abstracts, 20(1-2):1058 (1994).

Jarrett et al., "The Carboxy Terminus of the β Amyloid Protein is Critical for the Seeding of Amyloid Formation: Implications for the Pathogenesis of Alzheimer's Disease," *Biochemistry*, 32(18): 4693-4697 (1993).

Jensen et al., "Increased Cerebrospinal Fluid Tau in Patients with Alzheimer's Disease," *Neuroscience Letters*, 186:189-191 (1995).

Lannfelt et al., "Disease Progression Correlates with Decreasing CSF β Amyloid in Alzheimer Patients With the Swedish APP 670/671 Mutation," *Neurobiology of Aging*, 15(Suppl. 1):S79 (1994).

Pirttila et al., "Immunoreactivity Against Amyloid Beta Peptide (Aβ) is Decreased in the Cerebrospinal Fluid (CSF) from Patients with Alzheimer's Disease," *Neurology*, 44 (Suppl 2):315P (1994).

Press Release, Mayo Research Group, Mayo Researchers Identify a Good Predictor for Those at Greater Risk for Alzheimer's Disease (Jun. 19, 2005).

Selkoe, Dennis J., "Physiological production of the β-amyloid protein and the mechanism of Alzheimer's disease," *TINS*, 16(10): 403-409 (1993).

Shoji et al., "Production of the Alzheimer Amyloid β Protein by Normal Proteolytic Processing," *Science*, 258:126-129 (1992).

Society for Neuroscience Abstracts, vol. 20, Part 2 showing the date stamp for receipt by the British Library of May 1, 1995.

\* cited by examiner

METHODS FOR AIDING IN THE DIAGNOSIS OF ALZHEIMER'S DISEASE BY MEASURING AMYLOID-β PEPTIDE (X-≧41) AND TAU

This application is a divisional of Ser. No. 08/419,008, filed Apr. 7, 1995, now abandoned, which is a continuation-in-part of Ser. No. 08/339,141 filed Nov. 14, 1994, which are related to co-pending application Ser. No. 10/877,688 filed Jun. 25, 2004.

BACKGROUND OF THE INVENTION

1. Field of the Invention

The present invention relates generally to methods for diagnosing or monitoring Alzheimer's disease. More particularly, the present invention relates to measuring the amount of tau protein and/or the amount of β amyloid peptide (x-≧41) in patient fluid samples and using these amounts as a diagnostic indicator.

Alzheimer's disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in all races and ethnic groups worldwide and presents a major present and future public health problem. The disease is currently estimated to affect about two to three million individuals in the United States alone. AD is at present incurable. No treatment that effectively prevents AD or reverses its symptoms or course is currently known.

The brains of individuals with AD exhibit characteristic lesions termed senile plaques, and neurofibrillary tangles. Large numbers of these lesions are generally found in several areas of the human brain important for memory and cognitive function in patients with AD. Smaller numbers of these lesions in a more restricted anatomical distribution are sometimes found in the brains of aged humans who do not have clinical AD. Senile plaques and amyloid angiopathy also characterize the brains of individuals beyond a certain age with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure. The principal chemical constituent of the senile plaques and vascular amyloid deposits (amyloid angiopathy) characteristic of AD and the other disorders mentioned above is an approximately 4.2 kilodalton (kD) protein of about 39-43 amino acids designated the amyloid-β peptide (Aβ) or sometimes βAP, AβP or β/A4. Aβ was first purified and a partial amino acid sequence reported in Glenner and Wong (1984) Biochem. Biophys. Res. Commun. 120:885-890. The isolation procedure and the sequence data for the first 28 amino acids are described in U.S. Pat. No. 4,666,829. Forms of Aβ having amino acids beyond number 40 were first reported by Kang et al. (1987) Nature 325:733-736.

Roher et al. (1993) Proc. Natl. Acad. Sci. USA 90:10836-840 showed that Aβ(1-42) is the major constituent in neuritic plaques (90%) with significant amounts of isomerized and racemized aspartyl residues. The authors also showed that Aβ(17-42) also predominates in diffuse plaques (70%), while Aβ(1-40) is the major constituent in the meningovascular plaques, comprising 60% of the total Aβ and, in parenchymal vessel deposits Aβ(1-42) represents 75% of the total Aβ. Iwatsubo et al. (1994) Neuron 13:45-53 showed that Aβ42 (43)-positive senile plaques are the major species in sporadic AD brain.

Molecular biological and protein chemical analyses conducted during the last several years have shown that Aβ is a small fragment of a much larger precursor protein, referred to as the β-amyloid precursor protein (APP), that is normally produced by cells in many tissues of various animals, including humans. Knowledge of the structure of the gene encoding APP has demonstrated that Aβ arises as a peptide fragment that is cleaved from the carboxy-terminal end of APP by as-yet-unknown enzymes (proteases). The precise biochemical mechanism by which the Aβ fragment is cleaved from APP and subsequently deposited as amyloid plaques in the cerebral tissue and in the walls of cerebral and meningeal blood vessels is currently unknown.

Several lines of evidence indicate that progressive cerebral deposition of Aβ plays a seminal role in the pathogenesis of AD and can precede cognitive symptoms by years or decades (for review, see Selkoe (1994) J. Neuropath. and Exp. Neurol. 53:438-447 and Selkoe (1991) Neuron 6:487). The single most important line of evidence is the discovery in 1991 that missense DNA mutations at amino acid 717 of the 770-amino acid isoform of APP can be found in affected members but not unaffected members of several families with a genetically determined (familial) form of AD (Goate et al. (1991) Nature 349:704-706; Chartier Harlan et al. (1991) Nature 353:844-846; and Murrell et al. (1991) Science 254:97-99). Suzuki et al. (1994) Science 264:1336-1340 showed that in persons with the 717 mutation, there is a higher percentage of Aβ(1-42) than Aβ(1-40).

In addition, a double mutation changing lysine$^{595}$-methionine$^{596}$ to asparagine-$^{595}$-leucine$^{596}$ (with reference to the 695 isoform) found in a Swedish family was reported in 1992 (Mullan et al. (1992) Nature Genet. 1:345-347) and is referred to as the Swedish variant. Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the Aβ deposition disease, HCHWA-D, and a change from alanine to glycine at amino acid 692 appears to cause a phenotype that resembles AD in some patients but HCHWA-D in others. The discovery of these and other mutations in APP in genetically based cases of AD argues that alteration of APP and subsequent deposition of its Aβ fragment can cause AD.

Neurofibrillary tangles are composed mainly of the microtubule protein, tau. Z. S. Khachaturian (1985) Arch. Neurol. 42:1097-1105. Recent studies have shown that tau is elevated in the CSF of Alzheimer's disease patients. M. Vandermeeren et al. (1993) J. Neurochem. 61:1828-1834.

Despite the progress which has been made in understanding the underlying mechanisms of AD, there remains a need to develop methods for use in diagnosis of the disease. While the level of tau is of some help in diagnosing Alzheimer's disease (M. Vandermeeren et al., supra) more markers, and more specific markers would be helpful. It would be further desirable to provide methods for use in diagnosis of Aβ-related conditions, where the diagnosis is based at least in part on detection of Aβ and related fragments in patient fluid samples. Specific assays for Aβ detection should be capable of detecting Aβ and related fragments in fluid samples at very low concentrations as well as distinguishing between Aβ and other fragments of APP which may be present in the sample.

2. Description of the Background Art

Glenner and Wong (1984) Biochem. Biophys. Res. Commun. 120:885-890 and U.S. Pat. No. 4,666,829, are discussed above. The '829 patent suggests the use of an antibody to the 28 amino acid Aβ fragment to detect "Alzheimer's Amyloid Polypeptide" in a patient sample and diagnose AD. No data demonstrating detection or diagnosis are presented.

Numerous biochemical electron microscopic and immunochemical studies have reported that Aβ is highly insoluble in physiologic solutions at normal pH. See, for example, Glenner and Wong (1984) Biochem. Biophys. Res. Commun. 122:1131-1135; Masters et al. (1985) Proc. Natl. Acad. Sci. USA 82:4245-4249; Selkoe et al. (1986) J. Neurochem. 46:1820-1834; Joachim et al. (1988) Brain Research 474: 100-111; Hilbich et al. (1991) J. Mol. Biol. 218:149-163; Barrow and Zagorski (1991) Science 253:179-182; and Burdick et al. (1992) J. Biol. Chem. 267:546-554. Furthermore, this insolubility was predicted by and is consistent with the amino acid sequence of Aβ which includes a stretch of hydrophobic amino acids that constitutes part of the region that anchors the parent protein (APP) in the lipid membranes of cells. Hydrophobic, lipid-anchoring proteins such as Aβ are predicted to remain associated with cellular membranes or membrane fragments and thus not be present in physiologic extracellular fluids. The aforementioned studies and many others have reported the insolubility in physiologic solution of native Aβ purified from AD brain amyloid deposits or of synthetic peptides containing the Aβ sequence. The extraction of Aβ from cerebral amyloid deposits and its subsequent solubilization has required the use of strong, non-physiologic solvents and denaturants. Physiologic, buffered salt solutions that mimic the extracellular fluids of human tissues have uniformly failed to solubilize Aβ.

Separate attempts to detect APP or fragments thereof in plasma or CSF have also been undertaken. A large secreted fragment of APP that does not contain the intact Aβ region has been found in human cerebrospinal fluid (Palmert et al. (1989) Proc. Natl. Acad. Sci. USA 86:6338-6342; Weidemann et al. (1989) Cell 57:115-126; Henriksson et al. (1991) J. Neurochem. 56:1037-1042; Palmert et al. (1990) Neurology 40:1028-1034; and Seubert et al. (1993) Nature 361:260-263) and in plasma (Podlisny et al. (1990) Biochem. Biophys. Res. Commun. 167:1094-1101). The detection of fragments of the carboxy-terminal portion of APP in plasma has also been reported (Rumble et al. (1989) N. Engl. J. Med. 320: 1446-1452), as has the failure to detect such fragments (Schlossmacher et al. (1992) Neurobiol. Aging 13:421-434).

Despite the apparent insolubility of native and synthetic Aβ it had been speculated that Aβ might occur in body fluids, such as cerebrospinal fluid (CSF) or plasma (Wong et al. (1984) Proc. Natl. Acad. Sci. USA 92:8729-8732; Selkoe (1986) Neurobiol. Aging 7:425-432; Pardridge et al. (1987) Biochem. Biophys. Res. Commun. 145:241-248; Joachim et al. (1989) Nature 341:226-230; Selkoe et al. (1989) Neurobiol. Aging 10:387-395).

Several attempts to measure Aβ in CSF and plasma have been reported by both radioimmunoassay methods (WO90/12870 published Nov. 1, 1990) and sandwich ELISAs (Wisniewski in *Alzheimer's Disease*, eds. Becker and Giacobini, Taylor and Francas, N.Y. pg. 206, 1990; Kim and Wisniewski in *Techniques in Diagnostic Pathology*, eds. Bullock et al., Academic Press, Boston pg. 106; and WO90/12871 published Nov. 1, 1990). While these reports detected very low levels of Aβ immunoreactivity in bodily fluids, attempts to directly purify and characterize this immunoreactivity further and determine whether it represented Aβ were not pursued, and the efforts were abandoned. The possibility of Aβ production by cultured cells was neither considered nor demonstrated.

Retrospectively, the inability to readily detect Aβ in bodily fluids was likely due to the presence of amyloid precursor fragments with overlapping regions or fragments of Aβ that obscured measurements and to the lack of antibodies completely specific for intact Aβ. This is presumably because the antibodies used by both groups would cross-react with other APP fragments containing part of Aβ known to be present in CSF thereby interfering with the measurement, if any, of intact Aβ. These difficulties have been overcome with the use of monoclonal antibodies specific to an epitope in the central junction region of intact Aβ (Seubert et al. (1992) Nature 359:325-327).

Seubert et al. (1992) Nature 359:325-327 and Shoji et al. Science (1992) 258:126-129 provided the first biochemical evidence for the presence of discrete Aβ in bodily fluids. Vigo-Pelfrey et al. (1993) J. Neurochem. 61:1965-1968 reported the identification of many Aβ species in cerebrospinal fluid.

This application is related to U.S. patent application Ser. No. 07/965,972, filed Oct. 26, 1992, now abandoned; and U.S. patent application Ser. No. 08/079,511, filed Jun. 17, 1993, now U.S. Pat. No. 5,593,846, each of which is incorporated by reference.

SUMMARY OF THE INVENTION

The present invention provides methods useful for aiding in the diagnosis and monitoring of Aβ-related conditions in patients, where the methods rely on the specific detection in patient fluid samples of one or more soluble Aβ or soluble Aβ fragments having amino acid residues beyond number 40 in their carboxy-terminal end. These peptides are designated "Aβ(x-$\geq$41)" (Aβ from amino acid number "x" to an amino acid greater than or equal to amino acid number 41). In one embodiment, the measured peptides belong to the class of Aβ(x-$\geq$41) that contain at least amino acids 13-41.

For the diagnosis and monitoring of Aβ-related conditions, the amount of the aforementioned peptides in a patient fluid sample, especially cerebrospinal fluid (CSF), is measured and compared with a predetermined value, such as an indicator value (in the case of diagnosis) or a prior patient value (in the case of monitoring). In the case of diagnosis, measured amounts of Aβ(x-$\geq$41) which are above the indicator value are considered to be a strong indication that the patient is not suffering from AD or other Aβ-related condition. However, this information may also be considered together with other factors in making a determinative diagnosis. Measured amounts of Aβ(x-$\geq$41) which are at or below the indicator value are considered to be a positive indication that the patient may be suffering from AD or other Aβ-related condition. The low Aβ(x-$\geq$41) status of the tested individual usually will not by itself be considered a determinative diagnostic of an Aβ-related condition, but instead will be considered together with other accepted clinical symptoms of Aβ-related conditions in making a diagnosis. In cerebrospinal fluid, an indicator value of about 0.5 ng/ml is useful.

In a particular aspect, the present invention provides specific binding assays which are useful for detecting soluble Aβ(x-$\geq$41) in fluid samples and which may be employed in patient diagnostic and monitoring methods just described. Specific binding assays according to the present invention employ two binding substances specific for different epitopes or determinant sites on the Aβ(x-$\geq$41) molecule. One epitope or site is generally not found on other fragments or degradation products of the amyloid-β precursor protein (APP), so as to avoid cross-reaction with those fragments. Particularly useful are antibodies which recognize a junction region within Aβ, where the junction region is located about the site of normal proteolytic cleavage of APP between residues Lys[16] and Leu[17] (Esch et al. (1990) Science 248:492-495 and Anderson et al. (1991) Neuro. Science Lett. 128:126-128), typically spanning amino acid residues 13 to 26. The other epitope or site contains at least one amino acid beyond amino acid number 40 of Aβ that is essential for recognition, but does not cross-react with Aβ or Aβ fragments whose carboxy-terminal amino acid is number 40 or less. Exemplary specific binding assays include two-site (sandwich) assays in which the capture antibody is specific for the junction region of Aβ, as just described, and a second detectable antibody is specific for an epitope or site containing at least one Aβ amino acid beyond number 40. In particular, the second antibody can be produced by immunization with a hapten containing Aβ amino acids 33-42.

This invention also provides methods for aiding in the diagnosis or monitoring of Alzheimer's disease in a patient involving measurements of both Aβ(x-≧41) and the microtubule protein tau. The methods involve measuring the amount of one or more soluble Aβ(x-≧41) in a patient sample; comparing the measured amount with a predetermined amount of soluble Aβ(x-≧41); measuring the amount of tau in a patient sample; comparing the measured amount with a predetermined amount of said tau; and assessing patient status based on a difference between the measured and predetermined amounts of Aβ(x-≧41) and tau. Again, the predetermined amount can be an indicator value or a prior patient value. A measured amount at or below the Aβ(x-≧41) indicator value and at or above the tau indicator value provides a positive indication in the diagnosis of Alzheimer's disease, and wherein a measured amount above the of the Aβ(x-≧41) indicator value and below the tau indicator value provides a negative indication in the diagnosis of Alzheimer's-disease. Indicator values in the CSF of about 0.5 ng/ml for Aβ(x-≧41) and about 0.3 ng/ml for tau are useful.

This invention also provides kits for aiding in the diagnosis of Alzheimer's disease. The kits include a binding substance that binds Aβ(x-≧41) but that does not bind to Aβ(≦40) and a binding substance that binds to tau. In one embodiment, the kit contains four antibodies: a) an un-labeled antibody that binds to the junction region of Aβ; b) a detectably labelled antibody that binds to an epitope containing amino acids beyond number 40 in Aβ; c) an un-labelled antibody that binds to tau; and d) a detectably labelled antibody that binds to tau.

In another aspect, the present invention provides a system for detecting one or more soluble Aβ(x-≧41) in a fluid sample. The system includes a first binding substance, typically an antibody, specific for an epitope in a junction region of Aβ, as described above, and a second binding substance, typically an antibody, specific for an epitope of Aβ containing an amino acid beyond amino acid number 40 of Aβ at the carboxy-terminus essential for recognition. The first binding substance is an anti-Aβ antibody bound to a solid phase, while the other is a reporter antibody against the Aβ carboxy-terminus. The reporter antibody can, itself, be labeled, or can be detectable by another antibody (e.g., a rabbit antibody recognizable by labeled or enzyme-conjugated anti-rabbit antibodies.) The system can further include substrate for an enzyme label. The system is useful in performing enzyme-linked immunosorbent assays (ELISA) having high specificity and sensitivity for the detection of Aβ(x-≧41) in fluid samples.

In another aspect, this invention provides methods for screening a compound to determine its ability to alter the amount of Aβ(x-≧41) in the CSF. The methods involve measuring a first amount of soluble Aβ(x-≧41) in the CSF of a non-human animal used as a model of Alzheimer's disease; administering the compound to the non-human animal; measuring a second amount of soluble Aβ(x-≧41) in the CSF of the non-human animal; and comparing the first amount with the second amount. The difference indicates whether the compound increases Aβ(x-≧41) in the CSF, in which case it might be useful in the treatment of Alzheimer's; or decreases the amount, in which case the compound might aggravate or hasten Alzheimer's. The non-human animal preferably is a mammal, more preferably a rodent, and most preferably a mouse.

In another aspect, this invention provides methods for screening a compound to determine its ability to alter the amount of both Aβ(x-≧41) and tau in the CSF involving measuring a first amount of one or more soluble Aβ(x-≧41) in the CSF of a non-human animal used as a model of Alzheimer's disease; measuring a first amount of tau in the CSF of the non-human animal; administering the compound to the non-human animal; measuring a second amount of said one or more soluble Aβ(x-≧41) in the CSF of the non-human animal; measuring a second amount of tau in the CSF of the non-human animal; and comparing the first amounts with the second amounts, the difference indicating whether the compound increases, decreases, or leaves unchanged the amount of soluble Aβ(x-≧41) and increases, decreases, or leaves unchanged the amount of tau in the CSF. The information is useful, as above, to identify compounds that might be useful in treating Alzheimer's or that might aggravate or hasten Alzheimer's. The non-human animal preferably is a mammal, more preferably a rodent, and most preferably a mouse.

DESCRIPTION OF THE SPECIFIC EMBODIMENTS

The present invention results at least in part from the discovery that the cerebrospinal fluid ("CSF") of individuals suffering from Alzheimer's disease generally contains Aβ(x-≧41) in amounts which are in the very low end of the normal range present in the CSF of non-Alzheimer's individuals and, in particular, below about 0.5 ng/ml. This discovery is surprising because the bulk of Aβ deposits in the brain tissue of persons suffering from Alzheimer's disease is Aβ(1-42), and is significantly elevated compared to the amount of Aβ(1-42) in non-Alzheimer's individuals.

Based on this discovery the present invention provides methods for diagnosing and monitoring Alzheimer's disease. According to one method, a patient sample is first obtained. The patient sample is usually a fluid sample and, preferably, cerebrospinal fluid. Then the amount of soluble Aβ(x-≧41) in the patient sample is measured. A preferred method of measuring the amount is by using the sandwich assay described herein. The measured amount is then compared with a predetermined value, such as an indicator value in the case of diagnosis, or a prior patient value in the case of monitoring. The status of the patient is assessed based on the difference between the two amounts.

As described in more detail below, the methods of the present invention will be useful as both a positive and negative indicator of AD and other Aβ-related conditions in tested individuals. The data in the Experimental section show that individuals not suffering from Alzheimer's disease have CSF concentrations of soluble Aβ(x-≧41) that range from about 0.2 ng/ml to about 1.0 ng/ml. However, patients with Alzheimer's disease have CSF concentrations of soluble Aβ(x-≧41) generally below 0.5 ng/ml. Therefore, a measured amount above the indicator value of about 0.5 ng/ml is a very strong negative indication of Alzheimer's disease. That is, individuals having such levels are considered to be less likely to suffer from an Aβ-related condition and, in particular, Alzheimer's disease. An indicator value of 0.7 ng/ml will reduce the number of false negatives detected and is also useful as a predetermined amount. By contrast, a measured amount below the indicator value of 0.5 ng/ml is a positive indicator of Alzheimer's disease and individuals having these levels are considered to be more likely to suffer from Alzheimer's disease. An indicator value of 0.45 ng/ml reduces the number of false positives and is also useful as a predetermined value. However, since values below 0.5 ng/ml and 0.45 ng/ml are at the low end of the normal range found in non-Alzheimer individuals, a measured amount below the indicator level does not, by itself, suffice to provide a diagnosis of Alzheimer's disease. Therefore, the methods of the present invention will be useful as part of a diagnosis procedure which will also consider other known AD symptoms, such as those described in the NINCDS-ADRDA criteria (e.g., clinical dementia and memory impairment).

The invention also results in part from the discovery that a finding of Aβ(x-≧41) in the low end of the normal range together with a finding of higher than normal amounts of tau in the CSF of an individual is a stronger positive indicator of Alzheimer's disease than either finding alone, and that a finding of high levels of Aβ(x-≧41) and low levels of tau in the CSF of an individual is a very strong negative indicator of Alzheimer's disease. Thus, the combined use of these two markers appears to offer significant complementary diagnostic information.

Figure 6:
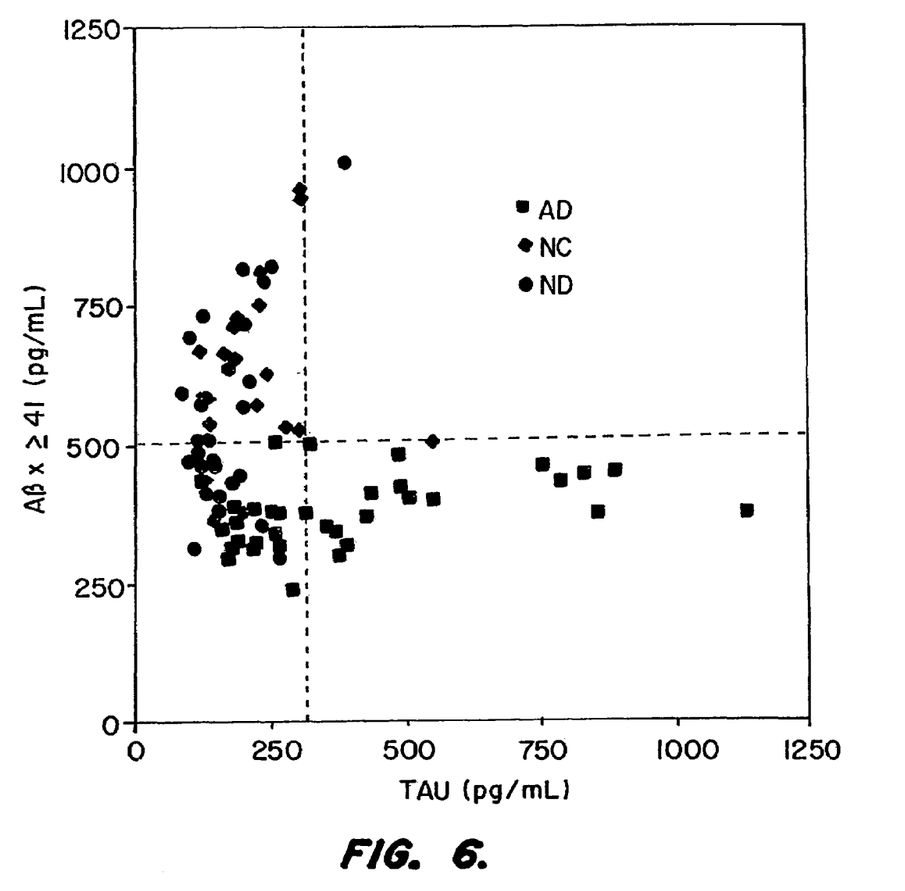
FIG. 6 shows the amounts of Aβ(x-≧41) and tau in CSF of Alzheimer's disease patients (AD), non-Alzheimer's neurological controls (ND) and non-demented controls (NC). Data from FIGS. 4 and 5 are combined to illustrate the effect of simultaneous consideration of the two measures in discriminating the AD group. Lines indicate optimized cut-offs. The high tau/low Aβ(x-≧41) quadrant contains AD patients with only a single exception (21/22 patients) whereas the low tau/high Aβ(x-≧41) quadrant contains only control individuals.

Data presented in FIG. 6 show that patients who exhibit high tau (above about 0.3 ng/ml) and low Aβ(x-≧41) (below about 0.5 ng/ml) had a 96% likelihood of having Alzheimer's disease (22/23). Fifty-nine percent of the Alzheimer's disease patients in this study (22/37) fall into this category. Conversely, patients who exhibit low tau (below about 300 ng/ml) and elevated Aβ(x-≧41) had a 100% likelihood of not having Alzheimer's disease (28/28, FIG. 6). Slightly over half of the non-Alzheimer's disease subjects (28/52, 54%) fall into this category. Taken together, the combined analysis of CSF tau and Aβ(x-≧41) was highly predictive of either the presence or the absence of Alzheimer's disease in slightly over half of all individuals enrolled in this study. The combined CSF tau and Aβ(x-≧41) measurements were not informative in those patients that fell into the low Aβ(x-≧41)/low tau group. Nevertheless, the ability of any test to aid in the inclusion or exclusion of Alzheimer's disease with high specificity and even moderate sensitivity is greatly important.

According to a second method of this invention, the amount of both soluble Aβ(x-≧41) and tau in a patient sample is measured. One useful method of determining the amount of tau is by ELISA as described in more detail below. The measured amounts of Aβ(x-≧41) and tau are then compared with pre-determined values for each. The status of the patient is assessed based on the difference between the pre-determined values and the measured values.

As discussed below, indicator values can be calibrated based on the particular binding substance used and the particular Aβ(x-≧41) and tau protein to be detected. Calibration involves testing the binding substance against standards from individuals having an Aβ-related disease and control standards from those not having such a disease. Indicator values are selected from these results based on the numbers of false positives or false negatives the practitioner is willing to tolerate. It is expected that indicator values using different binding substances and directed against the targets described herein will be roughly the same as the indicator values described herein. Indicator values below 0.45 ng/ml for Aβ(x-≧41) and above 0.4 ng/ml for tau decrease the number of false positive results; while indicator values above 0.7 ng/ml for Aβ(x-≧41) and below 0.25 ng/ml for tau decreases the potential for a false indication of freedom from Alzheimer's disease.

If the reason for reduced CSF Aβ(x-≧41) in AD is indeed secondary to ongoing plaque deposition, it could explain why a substantial number of neurological disease subjects and a few control subjects presented with low Aβ(x-≧41) levels in CSF. Plaque deposition has been hypothesized to precede cognitive failure and a significant portion of these elderly non-AD subjects would be expected to develop AD within the next several years (DMA Mann et al. (1992) Neurodegeneration 1:201-215 and DL Price et al. (1991) Neurobiol Aging 12:295-312). Longitudinal studies will obviously be required to address the possibility that low Aβ(x-≧41) levels are predictive of AD.

It was also found that levels of tau in AD CSF do not correlate with age, MMSE, total Aβ, Aβ$_{42}$, or ApoE ε4. Although the precise reason for elevation of tau in AD remains unclear, it is likely due to the increased tau levels in AD brain tissue (S. Khatoon et. al. (1992) J Neurochem 59:750-753) combined with the ongoing degeneration of neurons in the disease.

The sandwich assay described in the Experimental section used antibodies raised against the junction region of Aβ and against residues 33-42 of Aβ. In this assay, Alzheimer's patients generally had levels of Aβ(x-≧41) below 0.5 ng/ml as detected by the antibodies. The indicator value of 0.5 ng/ml is, in part, a function of the particular peptides recognized by the antibodies used as well as the peptide lot used in making the calibration. Therefore, the practitioner may base the predetermined amount on a re-calibration using reagents and protocols to be used in measuring Aβ(x-≧41) in the test.

In addition to initial diagnosis of the Aβ-related condition, the measured concentrations of Aβ may be monitored in order to follow the progress of the disease, and potentially follow the effectiveness of treatment (when such treatments become available). It would be expected that levels of Aβ(x-≧41) would decrease as the disease progressed.

The term "amyloid-β peptide," or "Aβ" as used herein refers to an approximately 4.2 kD protein which, in the brains of AD, Down's Syndrome, HCHWA-D and some normal aged subjects, forms the subunit of the amyloid filaments comprising the senile (amyloid) plaques and the amyloid deposits in small cerebral and meningeal blood vessels (amyloid angiopathy). Aβ 3 can occur in a filamentous polymeric form (in this form, it exhibits the Congo-red and thioflavin-S dye-binding characteristics of amyloid described in connection therewith). Aβ can also occur in a non-filamentous form ("preamyloid" or "amorphous" or "diffuse" deposits) in tissue, in which form no detectable birefringent staining by Congo red occurs. A portion of this protein in the insoluble form obtained from meningeal blood vessels is described in U.S. Pat. No. 4,666,829. Aβ is an approximately 39-43 amino acid fragment of a large membrane-spanning glycoprotein, referred to as the β-amyloid precursor protein (APP), encoded by a gene on the long arm of human chromosome 21. Forms of Aβ longer than 43 amino acids are also contemplated herein. Aβ is further characterized by its relative mobility in SDS-polyacrylamide gel electrophoresis or in high performance liquid chromatography (HPLC). A sequence for a 43-amino acid-version of Aβ is:

```
1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr [SEQ ID NO:1].
```

As used herein, Aβ also refers to related polymorphic forms of Aβ, including those that result from mutations in the Aβ region of the APP normal gene.

The term "Aβ fragment" as used herein refers to fragments and degradation products of Aβ which are generated at low concentrations by mammalian cells. Particular Aβ fragments have a molecular weight of approximately 3 kD and are presently believed to include peptides with, for example, amino acid residues 3-34, 6-27, 6-34, 6-35, 6-42, 11-34, 11-40, 17-40, 11-43 and 12-43 of Aβ.

As used herein, the term "Aβ(x-≧41)" refers to Aβ whose amino-terminus begins at amino acid number 1 of Aβ or which is truncated, and whose carboxy-terminus extends beyond amino acid number 40. These peptides and fragments comprise a heterogenous group. For example, Aβ(6-42), Aβ(11-43) and Aβ(12-43) all have been found in the CSF. However, this list is not meant to be exclusive. Other peptides from among the group are presumed to exist in the CSF and are detectable with the methods described herein.

The particular peptides measured from among the group of all Aβ(x-≧41) depends on the particular measuring method used. In the case of using binding substances, such as antibodies, the binding substance can be directed to one or more from among the group of peptides. For example, an antibody raised against amino acids 33-42 of Aβ that does not cross react with Aβ(1-40) will bind to Aβ(x-42). It also may bind to Aβ(x-41) and Aβ(x-43). According to one embodiment of the invention, the method involves determining the amount of Aβ(x-≧41) having at least amino acids 13-41 of Aβ. These species can be measured using a sandwich assay employing antibodies that recognize the junction region (amino acids 13-26) and antibodies produced by immunization with a hapten having Aβ amino acids 33-42, as described in the Example.

The term "Aβ junction region" as used herein refers to a region of Aβ which is centered at the site between amino acid residues 16 and 17 ($Lys^{16}$ and $Leu^{17}$) which is a target for proteolytic processing of APP. Such processing results in a variety of APP fragments which may, for example, terminate at amino acid 16 of Aβ and which, therefore, are potentially immunologically cross-reactive with antibodies to the intact Aβ molecule which are to be identified in the methods of the present invention. Antibodies raised against a synthetic peptide including amino acid residues 13-29 having been found to display the requisite specificity.

The term "amyloid-β precursor protein" (APP) as used herein is defined as a polypeptide that is encoded by a gene of the same name localized in humans on the long arm of chromosome 21 and that includes Aβ within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) Nature 325:733-736 which is designated as the "normal" APP; the 751-amino acid polypeptide described by Ponte et al. (1988) Nature 331:525-527 (1988) and Tanzi et al. (1988) Nature 331:528-530; and the 770-amino acid polypeptide described by Kitaguchi et al. (1988) Nature 331:530-532. Examples of specific variants of APP include point mutations which can differ in both position and phenotype (for review of known variant mutations see Hardy (1992) Nature Genet. 1:233-234).

The term "Aβ-related condition" as used herein is defined as including Alzheimer's disease (which includes familial Alzheimer's disease), Down's Syndrome, HCHWA-D, and advanced aging of the brain.

As used herein, "tau" refers to the family of microtubule-associated proteins. The paired helical filament of neurofibrillary tangles in the brains of Alzheimer's disease patients are composed of tau protein. (See, e.g., M. Goedert et al. (1989) Neuron 3:519-526 and M. Goedert (1993) TINS 16:460-465, incorporated herein by reference.) Goedert et al. (1989) also presents a DNA and amino acid sequence for tau.

The term "body fluid" as used herein refers to those fluids of a mammalian host which will be expected to contain measurable amounts of Aβ, Aβ fragments or tau protein, specifically including cerebrospinal fluid (CSF), blood, urine, and peritoneal fluid. The term "blood" refers to whole blood, as well as blood plasma and serum.

The methods and systems of this invention involve the ability to detect species of Aβ extending beyond amino acid number 40 at the carboxy-terminal end and, therefore, to distinguish them from shorter species, such as Aβ(40). While detection of Aβ(x-≧41) can be accomplished by any methods known in the art for detecting peptides, the use of immunological detection techniques employing binding substances such as antibodies, antibody fragments, recombinant antibodies, and the like, is preferred. Particularly suitable detection techniques include ELISA, Western blotting, radioimmunoassay, and the like. Suitable immunological methods employing a single antibody are also contemplated, for example, radioimmunoassay using an antibody specific for $\geq 41$ forms of A$\beta$, or single antibody ELISA methods.

Thus, this invention also provides antibodies specific for A$\beta$(x–$\geq$41) that do not cross react with A$\beta$($\leq$40). These antibodies can be made by immunizing animals with synthetic peptides that include amino acids beyond number 40 of A$\beta$. For example, the synthetic peptide can include amino acids 33-42. A specific example of the production of such an antibody is provided in the Experimental section.

According to one embodiment of the invention, detection and measurement of A$\beta$(x–$\geq$41) peptides involves the use of two antibodies, one specific for an epitope containing amino acids beyond number 40 in A$\beta$, and another antibody capable of distinguishing A$\beta$ and A$\beta$ fragments from other APP fragments which might be found in the sample. In particular, it has been found that antibodies which are monospecific for the junction region of A$\beta$ are capable of distinguishing A$\beta$ from other APP fragments. The junction region of A$\beta$ is centered at amino acid residues 16 and 17, typically spanning amino acid residues 13-26, and such junction-specific antibodies may be prepared using synthetic peptides having that sequence as an immunogen.

A preferred immunoassay technique is a two-site or "sandwich" assay employing a junction-specific antibody as the capture antibody (bound to a solid phase) and a second antibody which binds to an epitope containing amino acids beyond number 40 in A$\beta$. Particular methods for preparing such antibodies and utilizing such antibodies in an exemplary ELISA are set forth in the Experimental section hereinafter and in related U.S. Pat. No. 5,593,846.

Antibodies specific for A$\beta$ may be prepared against a suitable antigen or hapten comprising the desired target epitope, such as the junction region consisting of amino acid residues 13-29 and the carboxy terminus consisting of amino acid residues 33-42. Conveniently, synthetic peptides may be prepared by conventional solid phase techniques, coupled to a suitable immunogen, and used to prepare antisera or monoclonal antibodies by conventional techniques. Suitable peptide haptens will usually comprise at least five contiguous residues within A$\beta$ and may include more than six residues.

Synthetic polypeptide haptens may be produced by the well-known Merrifield solid-phase synthesis technique in which amino acids are sequentially added to a growing chain (Merrifield (1963) J. Am. Chem. Soc. 85:2149-2156). The amino acid sequences may be based on the sequence of A$\beta$ set forth above.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980, the disclosure of which is incorporated herein by reference. An exemplary immunogenic carrier utilized in the examples provided below is $\alpha$-CD3$_\epsilon$ antibody (Boehringer-Mannheim, Clone No. 145-2C11).

Once a sufficient quantity of the immunogen has been obtained, antibodies specific for the desired epitope may be produced by in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats, and the like. Immunogens are injected into the animal according to a predetermined schedule, and the animals are periodically bled, with successive bleeds having improved titer and specificity. The injections may be made intramuscularly, intraperitoneally, subcutaneously, or the like, and an adjuvant, such as incomplete Freund's adjuvant, may be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse, is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) Nature 256:495-497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in *Antibodies: A Laboratory Manual*, Harlow and Lane, eds., Cold Spring Harbor Laboratory, 1988, the full disclosure of which is incorporated herein by reference.

In addition to monoclonal antibodies and polyclonal antibodies (antisera), the detection techniques of the present invention will also be able to use antibody fragments, such as F(ab), Fv, $V_L$, $V_H$, and other fragments. In the use of polyclonal antibodies, however, it may be necessary to adsorb the anti-sera against the target epitopes in order to produce a monospecific antibody population. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

Detection of tau also can be accomplished by any methods known in the art for detecting peptides. However, the use of immunological detection techniques employing binding substances is preferred. Useful detection techniques include all those mentioned above. ELISA assays involving a capture antibody and a labeled detection antibody, both against tau, are particularly useful.

Antibodies against tau can be prepared by inoculating animals with tau purified from AD brains or from recombinant sources. Recombinant tau can be produced by expression in insect cells from a baculovirus vector containing pVL941-tau-4 repeat isoform as described by J. Knops et al. (1991) J Cell Biol 1991:114:725-733. Purified tau also is available from Immogenetics (Zwijndrecht, Belgium). Antibodies against tau are available from Sigma (St. Louis, Mo.). Additional sources can be identified in the Lindscott directory.

Tau can be prepared from AD brain by the method of Mercken et al. (1992) J Neurochem 58:548. Typically, 50 g of fresh brain is cut into small pieces with scissors and homogenized 1:1 (wt/vol) in buffer A (20 mM 2-[N-morpholino] ethanesulfonic acid, 80 mM NaCl, 2 mM EDTA, 0.1, mM EGTA, 1 mM MgCl$_2$, and 1 mM $\beta$-mercaptoethanol, pH 6.75) with a Potter homogenizer equipped with a Teflon plunger. The homogenate is centrifuged for 1 hour at 150,000 g at 4° C., and the supernatant is heated for 5 minutes in boiling water and chilled again for 10 minutes on ice. The slurry is centrifuged for 2 hours at 150,000 g at 4° C., and the supernatant is collected thereafter. The heat-stable cytosolic extract is made to 2.5% perchloric acid and centrifuged for 1 hour at 150,000 g at 4° C., after which the supernatant is neutralized with 3 M Tris. The supernatant is then dialyzed and concentrated in water in a Centiprep concentrator (Amicon, Lausanne, Switzerland). The end product can be evaluated in sodium dodecyl sulfate-polyacrylamide gel electrophoresis (SDS-PAGE) (Laemmli method). This preparation is useful for immunizing animals to produce anti-tau antibodies.

Tau also can be immunopurified from this preparation. Ten milligrams of anti-tau monoclonal antibody is coupled to 1 g of cyanogen bromide-activated Sepharose (Pharmacia) by the method proposed by the manufacturer. Fifty milliliters of the heat stable cytosolic extract described above is diluted 1:2 in 0.1 M phosphate buffer (pH 8.5) and applied to the column. The column is washed with 0.1 M phosphate, and tau is eluted with 0.1 M citric acid (pH 2.5) and neutralized immediately with 1 M NaOH. Fractions can be evaluated by SDS-PAGE on 10% gels and in immunoblotting with anti-tau antibodies.

This invention also provides kits for performing assays that aid in the diagnosis of Alzheimer's disease. The kits include means for detecting $A\beta(x-\geq 41)$ and means for detecting tau. The means can include any means known or described above, e.g., binding substances. Useful binding substances include molecules containing the binding portion of an antibody, such as a full antibody or an antibody fragment. The binding substances can be monoclonal antibodies. In one embodiment the kit includes a binding substance that binds $A\beta(x-\geq 41)$ but that does not bind to $A\beta(\leq 40)$ and a binding substance that binds to tau.

In one embodiment the kit includes antibodies or the like for performing sandwich ELISAs to detect each compound, for example, as described above. In one embodiment, the means to detect $A\beta(x-\geq 41)$ can include a binding substance that binds to an epitope containing amino acids beyond number 40 in $A\beta$ and a binding substance that binds $A\beta$ or a fragment of $A\beta$ but that does not bind other fragments of APP. The means to detect tau also can involve a sandwich ELISA. For example, the kit can include a) an un-labeled binding substance that binds to the junction region of $A\beta$; b) a detectably labelled binding substance that binds to an epitope containing amino acids beyond number 40 in $A\beta$; c) an un-labelled binding substance that binds to tau; and d) a detectably labelled binding substance that binds to tau.

The detectable labels can be any known and used in the art including, e.g., biotinylation, radioactive label, enzymes, fluorescent labels and the like.

Animal models are currently being used to study Alzheimer's disease. (See e.g., International Patent Application WO 93/14200 U.S. Pat. No. 5,604,102, and U.S. Pat. No. 5,387,742 all of which are incorporated herein by reference.) These models are useful for screening compounds for their ability to effect the course of Alzheimer's disease, both to ameliorate and aggravate the condition. Since AD is characterized by a decrease in the amounts of $A\beta(x-\geq 41)$ in the CSF, it is expected that effective treatments for Alzheimer's disease will result in an increase in amount of $A\beta(x-\geq 41)$ in the CSF, while agents that hasten progress of the disease will result in a decrease in the amount of $A\beta(\geq 41)$ in the CSF.

Accordingly, this invention provides methods for screening compounds that elevate or decrease the amount of $A\beta(x-\geq 41)$ in a fluid sample, in particular the CSF, and that, therefore, are candidates for use in treating the disease, or that hasten the disease and are to be avoided by humans. The methods involve measuring a first amount of said one or more soluble $A\beta(x-\geq 41)$ in a sample of a non-human animal used as a model of Alzheimer's disease; administering the compound to the animal; measuring a second amount of one or more soluble $A\beta(x-\geq 41)$ in a sample of the animal; and comparing the first amount with the second amount, the difference indicating whether the compound increases, decreases, or leaves unchanged the amount of soluble $A\beta(x-\geq 41)$ in the sample. The dosage level given to the animal and the amount of time that elapses before measuring the second amount will, of course, depend on the model system.

This invention also provides methods for screening compounds that elevate the amount of $A\beta(x-\geq 41)$ and decrease the amount of tau in a fluid sample, particularly CSF, and that, therefore, are candidates for use in treating the disease; or that decrease the level of $A\beta(x-\geq 41)$ and that increase the level of tau and therefore, that hasten the disease and are to be avoided by humans. The methods involve measuring a first amount of said one or more soluble $A\beta(x-\geq 41)$ and tau in a fluid sample of a non-human animal used as a model of Alzheimer's disease; administering the compound to the animal; measuring a second amount of one or more soluble $A\beta(x-\geq 41)$ and tau in a fluid sample of the animal; and comparing the first amounts with the second amounts, the difference indicating whether the compound increases, decreases, or leaves unchanged the amount of soluble $A\beta(x-\geq 41)$ and tau in the fluid sample. The dosage level given to the animal and the amount of time that elapses before measuring the second amount will, of course, depend on the model system.

One useful non-human animal model harbors a copy of an expressible transgene sequence which encodes the Swedish mutation of APP (asparagine$^{595}$-leucine$^{596}$). The sequence generally is expressed in cells which normally express the naturally-occurring endogenous APP gene (if present). Mammalian models, more particularly, rodent models and in particular murine and hamster models, are suitable for this use. Such transgenes typically comprise a Swedish mutation APP expression cassette, in which a linked promoter and, preferably, an enhancer drive expression of structural sequences encoding a heterologous APP polypeptide comprising the Swedish mutation.

The transgenic animals that harbor the transgene encoding a Swedish mutation APP polypeptide are usually produced by introducing the transgene or targeting construct into a fertilized egg or embryonic stem (ES) cell, typically by microinjection, electroporation, lipofection, or biolistics. The transgenic animals express the Swedish mutation APP gene of the transgene (or homologously recombined targeting construct), typically in brain tissue. Preferably, one or both endogenous APP allele is inactivated and incapable of expressing the wild-type APP.

The following examples are offered by way of illustration, not by way of limitation.

EXPERIMENTAL

I. $A\beta(x-\geq 41)$ is Decreased in Alzheimer's Patients

Materials and Methods

1. Antibody Preparation.

a. Monoclonal Antibodies to the $A\beta$ Junction Region.

Monoclonal antibodies to the junction region of $A\beta$ were prepared using a synthetic peptide spanning amino acid residues 13-31, except that AI, amino acids 30 and 31, were substituted with GC. This peptide was called Aβ$_{13-28}$. Aβ$_{13-28}$ was conjugated to an immunogen (α-CD3$_6$ antibody; Clone No. 145-2C11, Boehringer-Mannheim) using m-maleimidobenzoyl-N-hydroxysuccinimide ester (MBS) according to the manufacturer's (Pierce) instructions.

A/J mice were immunized initially intraperitoneally (IP) with the Aβ conjugate mixed with complete Freund's adjuvant. Fourteen days later, the mice were boosted IP with the Aβ conjugate mixed with phosphate buffered saline (PBS) at 14 day intervals. After six total boosts, the mice were finally boosted intravenously with Aβ conjugate mixed with incomplete Freund's adjuvant and fused 3 days later. Fusion of spleen cells with P3.653 myeloma cells was performed according as described in Oi and Herzenberg, *Selective Methods in Cellular Immunology*, Mishell and Shigii, Eds., W. H. Freeman and Company, San Francisco, Chapter 17 (1980). Serum titers and initial screens were performed by the RIA method described below. Several clones were expanded to a 24-well plate and subjected to further analysis as described below. Clones of interest were produced in mouse ascites.

The RIA method used to screen serum bleeds and fusion hybridoma supernatants was based upon a method developed by Wang et al. (1977) J. Immunol. Methods 18:157-164. Briefly, the supernatant (or serum) was incubated overnight at room temperature on a rotator with $^{125}$I-labeled Aβ$_{1-28}$ and Sepharose 4B beads to which sheep anti-mouse IgG had been coupled via cyanogen bromide. The beads from each well were harvested onto glass fiber filter discs with a cell harvester and washed several times with PBS. The filter discs were then transferred to gamma tubes and the bound radioactivity was counted in a gamma counter.

All hybridomas were tested for binding to Aβ$_{1-28}$ using the method described above in the initial screen, and then retested 3 days later. Aβ$_{1-28}$ positive clones were further characterized for reactivity to $^{125}$I-labeled Aβ$_{1-16}$ using the RIA method described above. No clones were found to bind Aβ$_{1-16}$. In a peptide capture ELISA, all clones were found to react with Aβ$_{13-28}$ while no clones reacted to Aβ$_{17-28}$ Therefore, it was determined that all clones had an epitope within the junction region spanning amino acids 16 and 17.

Based on results of the above assays, several clones were expanded into 24 well plates. These clones were further characterized by saturation analysis. Supernatants at the 50% titer point (as determined by the RIA method described above) were added to wells containing Sepharose™-sheep anti-mouse IgG beads, a constant amount of $^{125}$I-labeled Aβ$_{81-28}$, and varying amounts of unlabeled Aβ$_{13-28}$ or Aβ$_{17-28}$. The concentration of cold peptide for 50% inhibition was determined for each antibody. For the Aβ$_{17-28}$, no inhibition was seen at 100 ng/well for any clones. The 50% inhibition point for Aβ$_{13-28}$ ranged from 10-80 ng/well. The clones were also characterized based on reactivity in Western blots. Based on titer point, sensitivity (as determined by the 50% inhibition point), and reactivity on Western blot, several clones were produced in ascites. Antibodies from hybridoma designated 266 was selected for use as a capture antibody in the assays described below.

b. Polyclonal Antibodies to the C-Terminal Epitope Containing Amino Acids 33-42 of Aβ

Polyclonal antibodies were generated against Aβ(33-42) as follows. Peptide 277-2 (C-aminoheptanoic-GLMVGGVVIA [SEQ ID NO:2]) was conjugated to cationized BSA (Pierce activated "Supercarrier") at a ratio of 5 mg of 277-2 peptide to 10 mg of cationized BSA as follows. One vial of Pierce Supercarrier (10 mg) was resuspended in 1 mL of deionized water. 5 mg of the 277-2 peptide was dissolved in 5 ml of 10 mM PO$_4$ pH 8.0. The 277-2 peptide was added to the Supercarrier and incubated overnight at room temperature. This was then concentrated and the EDTA removed.

The immunogen (500 mg of peptide equivalent) was injected subcutaneously in complete Freund's adjuvant. Rabbits received a booster of 0.2-0.5 mg after three weeks and 0.2 to 0.5 mg at two to four week intervals thereafter. Boosters were subcutaneously administered in incomplete Freund's adjuvant. Twenty-five ml of serum was collected one week after each boost. Bleeds were screened as follows. Week 7 of the rabbit bleeds were titered by serial dilution. ELISA plates were coated with Aβ 1-42 overnight, and then blocked with 3% gelatin. Serial dilutions of the rabbit bleeds from 1/100-1/200,000 were incubated on the plates for 2 hours at room temperature. The plates were then washed and the anti rabbit HRP was added to each well. This incubated for one hour. The plate was washed and TMB substrate was used. ELISA titer of the rabbits was 1/20,000-1/200,000.

The ELISA positive rabbit bleeds were then titered in a capture RIA to compare its ability to capture $^{125}$I Aβ(1-42) versus $^{125}$I Aβ(1-40). Dilutions of rabbit antiserum from 1/25-1/675 were incubated with approximately the same number of cpm's of both tracers. Protein A sepharose was used to precipitate the immune complexes and they were then counted on a Microbeta scintillation counter. 277-2 rabbit D showed the highest titer to Aβ(1-42) tracer and no cross reaction with Aβ(1-40) tracer. The highest titer bleeds were then subjected to affinity purification of antibodies.

To affinity purity anti-277-2 antibodies, a 277-2 affinity matrix was prepared as follows: three ml of sulfo-link gel (Pierce) was washed with six volumes of 50 mM Tris, 5 mM EDTA, pH 8.5. Three mg of 277-2 peptide dissolved in 0.3 ml DMSO was brought to 3 ml with 50 mM Tris, 5 mM EDTA pH 8.5. and added to the gel. After gentle mixing for 15 minutes, the column resin was washed with six volumes of 50 mM Tris, 5 mM EDTA, 0.5 M NaCl pH 8. The column resin was then washed with 16 volumes of PBS/0.05% NaN$_3$.

To affinity purify the antibodies, 20 ml of high titer serum was diluted to 40 ml with PBS and an equal volume of saturated (NH$_4$)$_2$SO$_4$ was slowly added while stirring at 4°. The mixture was allowed to stir an additional 30 minutes then spun for 15 minutes at 10,000 rpm in a Beckman JA17 rotor. The pellets were resuspended in PBS, brought to a volume of 40 ml with PBS and the (NH$_4$)$_2$SO$_4$ precipitation repeated as above. The pellets were resuspended in a total of 20 ml of PBS and dialyzed overnight against PBS at 4°.

The 277-2 column was washed with 10 ml of PBS. Then the dialyzate was run over the column. The column was then washed with 50 ml of PBS. 0.1 M glycine, 0.5 M NaCl pH 2.5 was added 1 ml at a time and fractions collected. The first four fractions containing the majority of elated protein were pooled and neutralized with 0.4 ml of 1 M Tris pH 8.0. The pool was concentrated by membrane filtration to slightly less than 2 ml. The initial column flow-through was subjected to a second chromatographic step (after first neutralizing the column and re-equilibratihg it in PBS). The second affinity-purified material was similarly neutralized and concentrated, combined with the first material and then dialyzed against PBS overnight, 40. The protein content was determined (Pierce BCA method) and these antibodies were used in ELISA experiments.

c. Monoclonal Antibodies to the N-Terminal Region of βAP.

Monoclonal antibodies to the N-terminal region of βAP were prepared using a synthetic peptide spanning amino acid residues 1-28 (βAP$_{1-28}$). βAP$_{1-28}$ was chemically coupled using disuccimidyl suberate (DSS) to rabbit serum albumin (RSA) using a 20:1 molar ratio of peptide to protein in 50 mM sodium phosphate, pH 7.0, 150 mM NaCl, overnight at 21° C. using 1 mM DSS (Hyman et al. (1992) J. Neuropath. Exp. Neuro. 51:76).

Antibodies 10D5 and 6C6 were obtained from a fusion where mice had received 5 injections of $\beta AP_{1-28}$ coupled to RSA via DSS at 100 µg/ml. The initial injection was in complete Freund's adjuvant (CFA) followed by second and subsequent injections in incomplete Fruend's adjuvant (IFA) every 10-14 days. Three days before the fusion, mouse 4 which had a titer of 1/70,000 as measured by ELISA against $\beta AP_{1-28}$, received 100 µg of $\beta AP_{1-28}$ RSA in PBS intraperitoneally as a final boost. Screening was done by ELISA and on paraffin-fixed AD brain sections. The coating concentration of $\beta AP_{1-28}$ was 1 µg/well. 10D5 and 6C6 were positive by ELISA and AD brain tissue section.

2. ELI Assay.

a. Binding of Capture Antibody to Microtiter Wells.

Monoclonal antibody 266 was diluted to a concentration of 10 µg/ml in a buffer containing 0.23 g/L $NaH_2PO_4H_2O$, 26.2 g/L $Na_2HPO_4$; $7H_2O$, 1 g/L $NaN_3$, pH 8.5. One hundred µl/well of this solution was then dispensed in a 96 well white Dynatech Microlite 2, 96 well flat-bottomed plate. The plates were sealed and incubated overnight at room temperature. Following coating, the remaining solution was aspirated and the non-specific binding sites were blocked with 200 µL per well of $(NaH_2PO_4H_2O)$ 0.2 g/L, $Na_2HPO_4.7H_2O$ 0.8 g/L, human serum albumin (HSA) crystallized and lyophilized 2.5 g/L, pH 7.4. These plates were blocked by incubating for 1 hour at room temperature in the blocking solution.

b. Assay Protocol.

The calibrators were prepared from a stock solution of $A\beta_{1-42}$, 1 µg/ml, in DMSO. In specimen diluent $((NaH_2PO_4.H_2O)$ 0.2 g/L, $Na_2HPO_4.7H_2O$ 2.16 g/L, $NaN_3$ 0.5 g/L, bovine serum albumin (BSA) (globulin free) 6 g/L, triton x-405 0.5 ml/L NaCl 8.5 g/L, pH 7.4.), the highest calibrator, 1000 pg/ml (10 µl $A\beta_{1-42}$ stock (1 g/ml DMSO) in 10 ml casein specimen diluent) was prepared. Sequential dilutions were made in specimen diluent to obtain 500, 250, 125, 62.5 and 31.25 pg/ml concentrations of $A\beta_{1-42}$.

CSF samples were prepared as follows. The CSF samples (100-500 µl) were boiled for 3 minutes. The boiled samples were placed at 4° C. for 10-14 hours before assaying. CSF samples are assayed undiluted. Dilutions are only made if the initial calculated value is above the highest calibrator (1000 pg/ml).

One hundred µL per well calibrators or samples were applied to the microtiter plates. The plates were sealed and incubated for 1 hour at room temperature. The plates were then washed three times with washing buffer (NaCl 80 g/L, KCl 3.85 g/L, Tris-HCl 31.75 g/L, tween-20 0.5 ml/L, pH 7.5).

Anti-Aβ(33-42) (antibody 277-2) was diluted in specimen diluent to 1 g/ml and 100 µl was added per well. The plate was covered and incubated for 1 hour at room temperature. The plate was washed three times with washing buffer. The alkaline phosphatase affinity purified F(ab')2 fragment donkey anti-rabbit IgG (H+L) (Jackson) was diluted 1:1000 in specimen diluent. One hundred µl/well was added. The plate was covered and incubated for 1 hour at room temperature. The plate was washed three times with washing buffer, then 100 µl/well of chemiluminescent substrate was added. The chemiluminescent substrate was prepared by diluting the chemiluminescent reagent, AMPPD (Tropix), and an enhancer, emerald green (Tropix), 1:1000 and 1:100 respectively in 1M diethanolemine buffer, pH 10, containing 1 mM $MgCl_2$ and 0.2% $NaN_3$. The plates were sealed and incubated for 10 to 15 minutes at room temperature. Solution was not aspirated. This time may have to be optimized for different antibody lots.

Chemiluminescence was read and expressed as relative chemiluminescence units (CLU) after 15 minutes using a Dynatech ML 1000.

Results

1. Aβ(x-≧41) Assay Specificity

Figure 1:
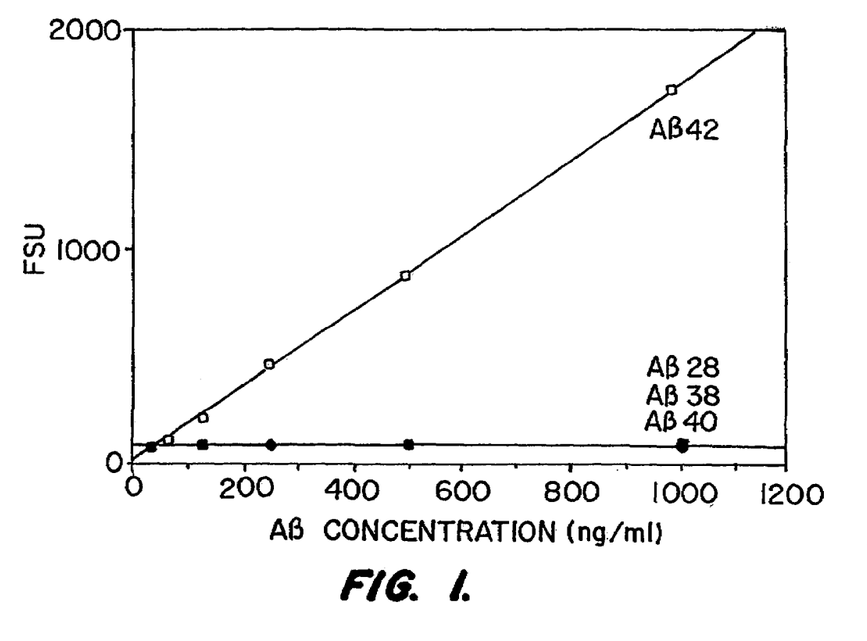
FIG. 1 shows the results of ELISA assays using antibody 266 (directed to the Aβ junction region) and antibody 277/2 (directed to Aβ amino acids 33-42) to detect Aβ(42), but not Aβ(28), Aβ(38), or Aβ(40).

Aβ(x-≧41) ELISA does not cross-react with Aβ(1-28), (1-38), or (1-40) (FIG. 1).

2. Aβ(x-≧41) Assay Sensitivity

The lower sensitivity limit for this assay is 31 pg/ml or 3.1 pg/well (0.7 fmol/well) (FIG. 1).

3. Aβ(x-≧41) Levels in CSF

Figure 2:
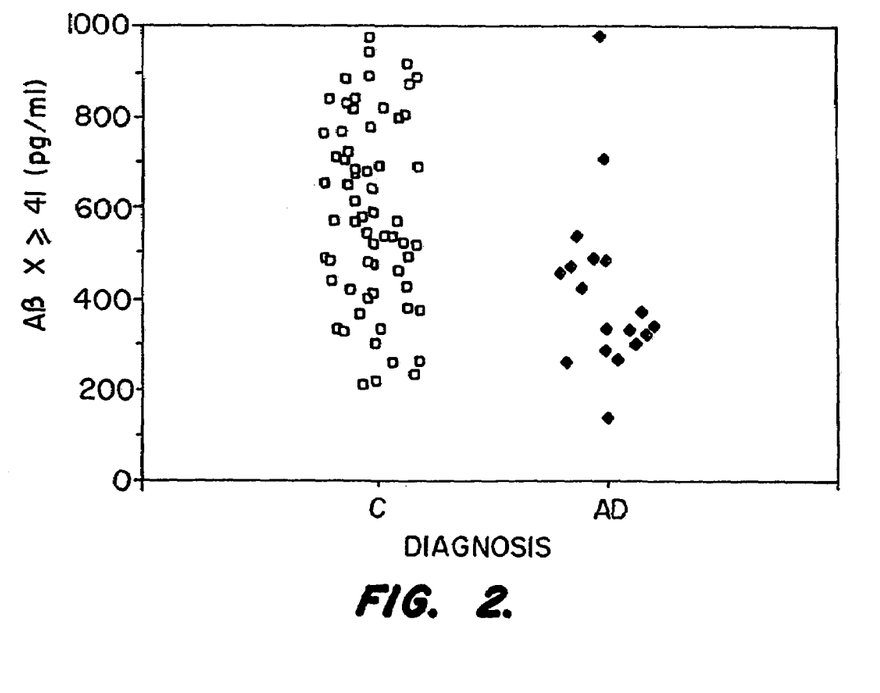
FIG. 2 shows the amounts of Aβ(x-≧41) in CSF of control patients (C) and AD patients (AD) in Group A as detected by ELISA.
Figure 3:
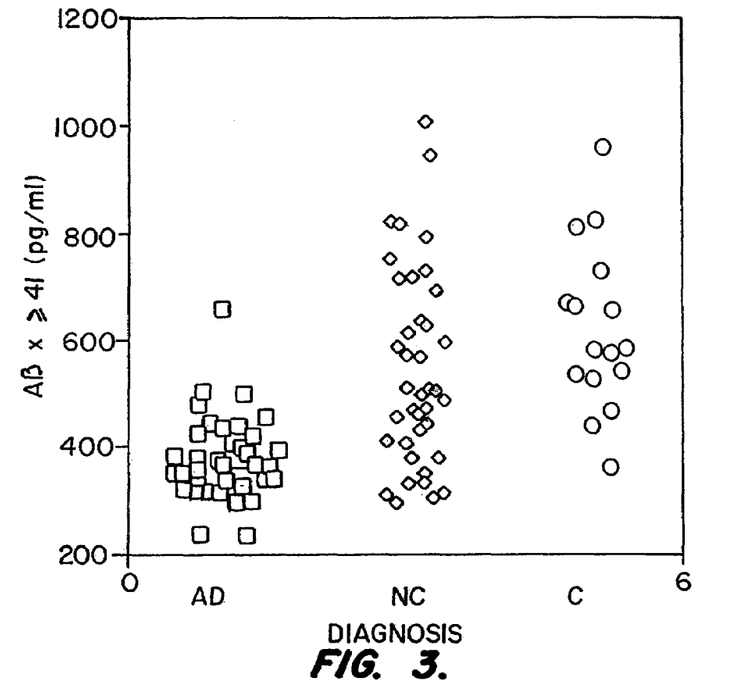
FIG. 3 shows the amounts of Aβ(x-≧41) in CSF of AD patients (AD), non-Alzheimer's neurological controls (NC) and controls (C) in Group B as detected by ELISA.

Aβ(x-≧41) has been verified in CSF using the Aβ(x-≧41) ELISA. On occasion, two different groups of CSF samples, designated Group A and Group B, were obtained from various sources. Sometimes, two hundred µL of the CSF samples were boiled for 3 minutes prior to assay (boiling was found to increase Aβ(x-≧41) immunoreactivity in some cases). The results of this assay can be seen in FIG. 2 and FIG. 3. Table 1 summarizes these results.

TABLE I

AD DIAGNOSTICS Aβ (x - ≧41) Data Groups A and B CSF

| GROUP | Aβ1-42 (pg/mL) CUTOFF | SENSITIVITY FOR AD* | SPECIFICITY FOR AD |
|---|---|---|---|
| Group A | ≦362.7 | 50% | 84% |
|  | ≦588.0 | 93.8% | 50.0% |
| Group B | ≦367.4 | 50% | 85% |
|  | ≦504.4 | 97.4% | 56.6% |

*Equal to specificity for detecting that an individual does not have AD.

4. Aβ(x-≧41) in CSF of Rodents and Dogs

Aβ(x-≧41) immunoreactivity was also detected in CSF of guinea pigs and dogs (Table II).

TABLE II

Aβ IMMUNOREACTIVITY IN THE CSF OF VARIOUS ANIMAL SPECIES

| SPECIES | TOTAL Aβ (ng/ml) | Aβ (x - ≧41) (ng/ml) | % Aβ (x - ≧41) |
|---|---|---|---|
| Guinea Pig | 4.5 | 0.242 | 5.4 |
| Dog | 4.4 | 0.59 | 13.4 |

This sandwich ELISA demonstrates the presence of Aβ(x-≧41) in CSF. Aβ(x-≧41) is only a minor component of the total Aβ in CSF. The levels of Aβ(x-≧41) in CSF are significantly lower in AD than normal and neurological controls. Taking a 50% sensitivity limit, the specificity is 93.8 for Group A and 97.4% for Group B. These two independent groups show a remarkable similarity demonstrating that measurements of Aβ(x-≧41) in CSF have diagnostic utility.

II. Combined Measurements of Aβ(x–≧41) and Tau are Highly Sensitive for Alzheimer's Disease Materials and Methods 1. Subjects All subjects enrolled in this study underwent detailed clinical and neurological evaluation at university medical centers by neurologists expert in the diagnosis of dementia. Informed consent was obtained from subjects, or their guardians, as appropriate. The evaluation included medical history, physical and neurological examinations, laboratory blood tests to exclude metabolic causes of dementia, a neuroimaging study (head CT or MR within the past 3 years for demented patients and neurological controls), and detailed psychometric testing (this varied between institutions). In addition, all subjects received the following assessment instruments: the Mini-Mental State Examination (MMSE) (American Psychiatric Association, Committee on Nomenclature and Statistics: Diagnostic and Statistical Manual of Mental Disorders: Revised Third Edition, Washington D.C. Am. Psych Associ. (1987)), the Hamilton Depression Inventory (V. C. Hachinski et al. (1975) Ann Neurol 32:632-637) and the Hachinski Ischemic Index (G. McKann et al. (1984) Neurology 34:939-944). Patients with more than one dementia diagnosis, recent stroke, head trauma, or significant peripheral nervous system disorders were excluded. The following diagnostic criteria were used:

i. AD (n=37): patients met NINCDS-ADRDA guidelines for probable AD; those who met criteria for possible AD were excluded (The Lund and Manchester Groups (1994) J Neurol Neurosurg Psychiatr 57:416-418). All patients were community dwelling and had mild to moderate dementia.

ii. Neurological disease controls (ND; n=32): patients with non-AD dementia or degenerative disorders affecting the central nervous system. For neurological controls, a summary of clinical records was also reviewed by a second neurologist (DG) to confirm diagnoses and to ensure that co-existing AD was unlikely. Patients with frontal lobe dementia were diagnosed according to the criteria set forth by the Lund and Manchester groups (Kawasaki E. S., in: PCR Protocols: A guide to methods and applications. Academic Press, Inc., New York 1990 pp. 146-152).

iii. Non-demented controls (NC; n=20): Subjects were age 50 or older and lacked significant cognitive complaints, did not have functional impairment, had normal findings on neurological examination, and scored 28-30 on the MMSE. A subgroup of these controls had symptoms of depression that did not result in significant cognitive or functional impairment, and were judged not to have AD or any organic neurological condition.

Lumbar punctures were performed in the mornings, after an overnight fast. All CSF samples were collected into specimen tubes provided to all sites. The first 2-3 ml of CSF was analyzed for protein, glucose and cells at the local medical center laboratory, and 4.5 mL were removed from original collection tubes and added to 8 mL Sarstedt tubes containing 500 μL buffer (containing additives such that the final CSF solution composition included: 20 mM sodium phosphate, 20 mM triethanolamine, 0.05% Triton X-100, 100 mM NaCl, 0.05% $NaN_3$, 1 mM diethylene triamine penta acetic acid, 1 mM EGTA, pH 7.4) and frozen at –20° C. until analysis. Assay operators were unaware of the subjects' diagnoses.

2. ApoE Genotyping

ApoE genotyping was performed on available blood samples, which had been collected into EDTA vacutainer tubes. Samples were prepared by the method of Kawasaki (Kawasaki E S, in: *PCR Protocols: A guide to methods and applications*, Academic Press, Inc., New York 1990 pp. 146-152) and PCR analysis performed as described by Wenham (P. R. Wenham et al. (1991) Lancet 337:1158-1159).

3. Total Aβ ELISA

Total Aβ was measured in a sequential double monoclonal antibody sandwich ELISA as described in Seubert et al. (1992) Nature 359:325-327. Briefly, Aβ in CSF was captured by monoclonal antibody 266 (specific for Aβ peptide residues 13-28) which had been pre-coated in microtiter plate wells. Detection utilized a second Aβ specific, biotinylated monoclonal antibody 6C6 (recognizing Aβ residues 1-16), followed by reaction with an alkaline phosphatase-avidin conjugate. After incubation with the fluorogenic substrate 4-methyl-umbellipheryl phosphate (MUP), the fluorescent product was measured using a Millipore Cytofluor 2350 fluorometer.

4. Aβ(x–≧41) ELISA

Aβ(x–≧41) was measured in a similarly formatted assay using 266 as the capture antibody. The reporter polyclonal antibody 277-2 was raised against a synthetic peptide which included Aβ residues 33-42 (GLMVGGVVIA) [SEQ ID NO:2], with cysteine-aminoheptanoic-acid at its amino-terminus. It was conjugated through the cysteine to cationized BSA (Pierce) The antibody 277-2 was affinity purified using the synthetic peptide conjugated to Sulfo-link resin (Pierce) and reacted strongly with $^{125}$I-Aβ$_{1-42}$ as detected by precipitation of tracer. It showed no detectable cross-reactivity with Aβ$_{1-40}$ in either immunoprecipitation or ELISA formats, indicating at least a 1,000-fold less sensitivity towards the Aβ 1-40 peptide. Synthetic Aβ$_{1-42}$ was used as the standard. Detection of the 277-2 reporter antibody was achieved using a donkey anti-rabbit IgG-alkaline phosphatase conjugate and the AMPPD chemiluminescent substrate with Emerald enhancer (Tropix) (C. Vigo-Pelfrey et al. (1994) J Neurochem 61:1965-1968).

To eliminate inter-assay variability as a factor in the Aβ(x–≧41) analysis, all samples were run in duplicate on the same day with the same lot of standards. The intra-assay variability was less than 10%. Prior to measure, aliquots of CSF samples were heated to 100° C. for three minutes and then stored at 40 overnight before assay. The heating step was found to generally increase immunoreactivity in CSF samples, independent of diagnosis, and was therefore included. It should be noted that different lots of synthetic Aβ(x–≧41) generate slightly different standard values, despite being normalized by amino acid analysis. Values listed are based upon a single standard used for the entire study. Studies involving addition of synthetic Aβ(x–≧41) to CSF demonstrated that measured recovery was 80±5%.

5. Detection of Tau by ELISA a. Purified Tau

Tau purified from human AD brain tissue and from recombinant sources were used for characterization of the assay and antibodies. Recombinant human tau was produced using the previously described baculovirus vector containing the pVL941-tau-4-repeat isoform (J. Knops et al. (1991) J Cell Biol 1991:114:725-733). High levels of tau were expressed and purified from both SF9 and high five insect cells. Maximally expressing cell cultures were harvested, washed once in PBS, and chilled on ice. The cells were then sonically disrupted in 0.1 M MES pH 6.5, 1 mM EGTA, 18 μM EDTA, 0.5 mM $MgCl_2$, 5 μg/ml leupeptin, 1 mM PMSF. Cell debris was removed by low speed centrifugation and the supernatant adjusted to 0.75 M NaCl, 2% β-mercaptoethanol. The samples were boiled 10 minutes in capped tubes, cooled in ice and clarified by centrifugation at 100,000×g for 30 minutes. The supernatants were then adjusted to 2.5% perchloric acid and spun for 15 minutes at 13,000×g. The pellets were subjected to a second cycle of boiling/acid precipitation and the pooled supernatants were dialyzed against 100 mM $KH_2PO_4$ pH 6.9, 2 mM EDTA, 2 mM EGTA, 2 mM β-mercaptoethanol, 0.3 mM PMSF.

The recombinant tau was judged to be at least 85% pure by SDS-PAGE stained with Coomassie blue and was used without further purification. The concentrations of all tau standards were estimated by amino acid analysis. To dephosphorylate tau, an aliquot was dialyzed into 20 mM Tris-HCl pH 8.6, 2 mM $MgCl_2$, 1 mM DTT, 10 μM $ZnCl_2$ buffer. To half of the sample, 0.1 units of alkaline phosphatase (Boehringer Mannheim) per μg-tau were added; the other half was similarly diluted with buffer alone and the two samples were incubated from 5 hours at 37°.

b. Monoclonal Antibodies Against Tau

Monoclonal antibodies were prepared according to a modification of the method of Kohler and Milstein (G. Kohler and C. Milstein (1975) *Nature* 256:495-497). Tau used in all injections and screening assays was purified from SF9 cells infected with the tau-containing baculovirus construct. Six week old A/J mice were injected with 100 μg of purified tau at two week intervals. Tau was emulsified in complete Freund's adjuvant for the first immunization and in incomplete Freund's adjuvant for all subsequent immunizations. Serum samples were taken three days after the third injection to assess the titer of these animals. The highest titer mouse was injected intravenously with 100 μg of tau in 500 μL of PBS two weeks after receiving its third injection. The myeloma fusion occurred three-days later using SP2/0 as the fusion partner. Antibodies 16G7 and 8C11 were obtained from this fusion while antibodies 16B5 and 16C5 were isolated from a subsequent fusion.

Supernatants from wells containing hybridoma cells were screened for their ability to precipitate $^{125}$I-labeled tau. Tau was radio-iodinated using immobilized glucose oxidase and lactoperoxidase according to the manufacturer's instructions (Bio-Rad). Briefly, 10 μg of purified recombinant tau was radiolabeled with 1 mCi of $Na^{125}I$ to a specific activity of 20 μCi/μg protein. 16G7, 8C11, 16B5 and 16C5 were identified as the four highest affinity monoclonal antibodies specific to tau and were cloned by limiting dilution. The isotypes on all four monoclonal antibodies specific to tau were determined to be gamma 1 kappa.

c. Tau ELISA

The anti-tau monoclonal antibody 16G7 was suspended at 5 μg/ml in TBS and 100 μl/well coated into microtiter plates (Dynatec Microlite 2). The coating was carried out overnight at room temperature. The solution was then aspirated and the plates blocked with 0.25% casein (w/v) in phosphate buffered saline (PBS). The anti-tau antibody 16B5 was biotinylated with the N-hydroxysuccinimide ester of biotin following the manufacturer's instructions (Pierce). Samples of either 50 μl CSF or calibrators (50 μl of 3-1000 pg/ml human tau), were combined with 50 μl of the biotinylated anti-tau antibody (0.75 μg/ml in PBS-casein, 0.05% Tween 20) into the 16G7 coated wells and incubated overnight at room temperature with constant shaking. The solution was then aspirated and plates washed three times in TTBS. Streptavidin alkaline phosphatase (Boehringer-Mannheim) was diluted 1:1000 in PBS-casein, 0.05% Tween 20 and 100 μl added to each well. After incubation for 1 hour at room temperature, the fluid was aspirated and wells washed three times. The chemiluminescent reagent, disodium 3-(4-methoxyspiro{1,2-dioxetane-3, $2^1$-tricyclo [$3.3.1.1^{3,7}$] tdecan}-4-yL) phenyl phosphate (AMPPD, Tropix) and an enhancer Emerald green (Tropix) were diluted 1:1000 and 1:100 respectively in 1 M diethanolamine buffer, containing 1 mM $MgCl_2$, 0.02% $NaN_3$, pH 10. 100 μl were added per well and the plates were read after 30 min. in a Dynatech ML 1000 chemiluminometer. The data reported here used human tau isolated from brain as the calibrator.

6. Statistical Analysis

Statistical analysis of data was performed by one way analysis of variance (ANOVA) using InStat, Version 1.21.

Results

Comparison of the three patient groups (Table III) showed that they were well matched for age and gender. The AD group had an average MMSE of 17.5±7.1 indicating mild to moderate cognitive impairment. The neurological disease control group consisted of a variety of disorders including vascular dementia (4), frontal lobe dementia (7), depression (6), Parkinson's disease (3), cortico-basal ganglionic degeneration (2), cerebellar ataxia (2), progressive supranuclear palsy (1), normal pressure hydrocephalus (1), grand mal seizure (1), Bell's palsy (1), age-associated memory impairment (1), dementia with extrapyramidal signs (1), amnestic syndrome (1), cerebellar degeneration (1). The control group consisted of individuals who were free of neurological disease and were cognitively normal (Table III).

TABLE III

SUMMARY OF PATIENT PROFILES AND MEASURED PARAMETERS

| | Alzheimer's Disease (AD) | Neurological Controls (ND) | Normal Controls (NC) |
|---|---|---|---|
| n | 37 | 32 | 20 |
| Age (mean ± SD) | 70 ± 9.1 | 66 ± 9.1 | 70 ± 6.2 |
| Sex (M %/F %) | 48.6/51.4 | 59.4/40.6 | 50/50 |
| MMSE (mean ± SD) | 17.5 ± 7.1 | 23 ± 8.2 | 29.5 ± 0.6 |
| CSF Aβ (mean ± SD, ng/ml) | 19.0 ± 6.9 | 17.9 ± 6.7 | 21.8 ± 6.9 |
| APOEε4 frequency[1] | 0.58 | 0.26 | 0.21 |
| $Aβ_{42}$ (mean ± SD, pg/ml) | 383 ± 76** | 543 ± 177 | 632 ± 156 |
| Tau (mean ± SD, pg/ml) | 407 ± 241* | 168 ± 63 | 212 ± 102 |

[1]ApoE genotypes were determined on 30/37 AD, 19/32 neurological control and 17/20 normal controls.
**p <.0001 comparing AD group to either control group.
*p <.001 comparing AD group to either control group.

Figure 4:
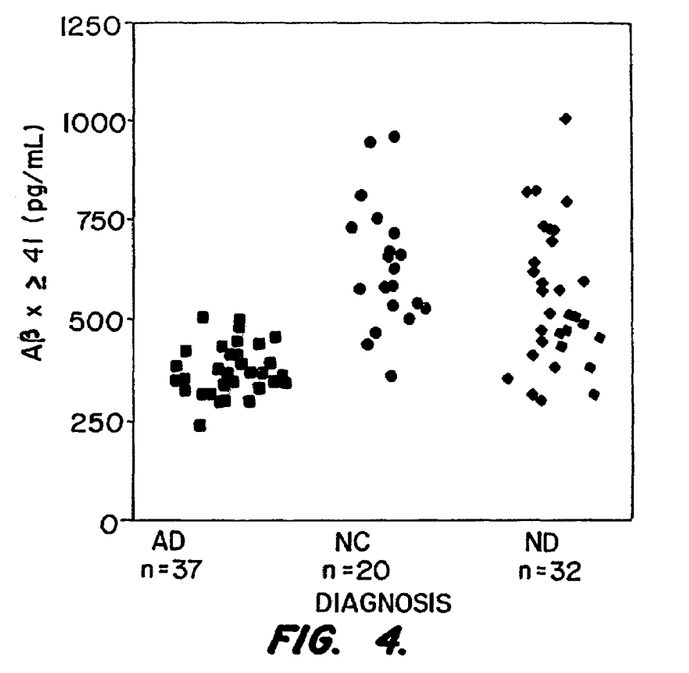
FIG. 4 shows the amounts of Aβ(x-≧41) in CSF of AD patients (AD), non-Alzheimer's neurological controls (ND) and non-demented controls (NC) as detected by ELISA.

Analysis of total CSF Aβ levels revealed no significant differences among the different patient groups (Table III). The mean values ranged from 19.0 ng/ml in the AD group to 17.9 ng/ml in the NC group. There was significant overlap with no statistically significant differences among the groups (p>0.05). Analysis of the Aβ(x–≧41) form of the peptide, however, demonstrated a reduction in the mean value in the AD group, relative to both the ND and NC subjects (383 versus 543 and 632 pg/ml respectively) that was significant at the p<0.0001 level (FIG. 4). The relatively small standard deviation (76 pg/ml) of the AD group was particularly striking. Conversely, some of the ND patients exhibited reduced Aβ(x–≧41) in their CSF. When a cutoff was set at 505 pg/ml, 15 of 37 ND patients and only four of 23 NC fell below this level. Alternatively, of the 35 individuals that have levels of Aβ(x–≧41) greater than 505 pg/ml, none was diagnosed with AD, suggesting the test is highly specific for the absence of disease. Aβ(x-≧41) was measured as described in the text. All measures are the averages of duplicate determinations, variation was ≦10%. Samples were assigned randomly to plates and the operator was unaware of the subject diagnoses. Reference standards, present on each microtiter plate, were not significantly different between plates.

Figure 5:
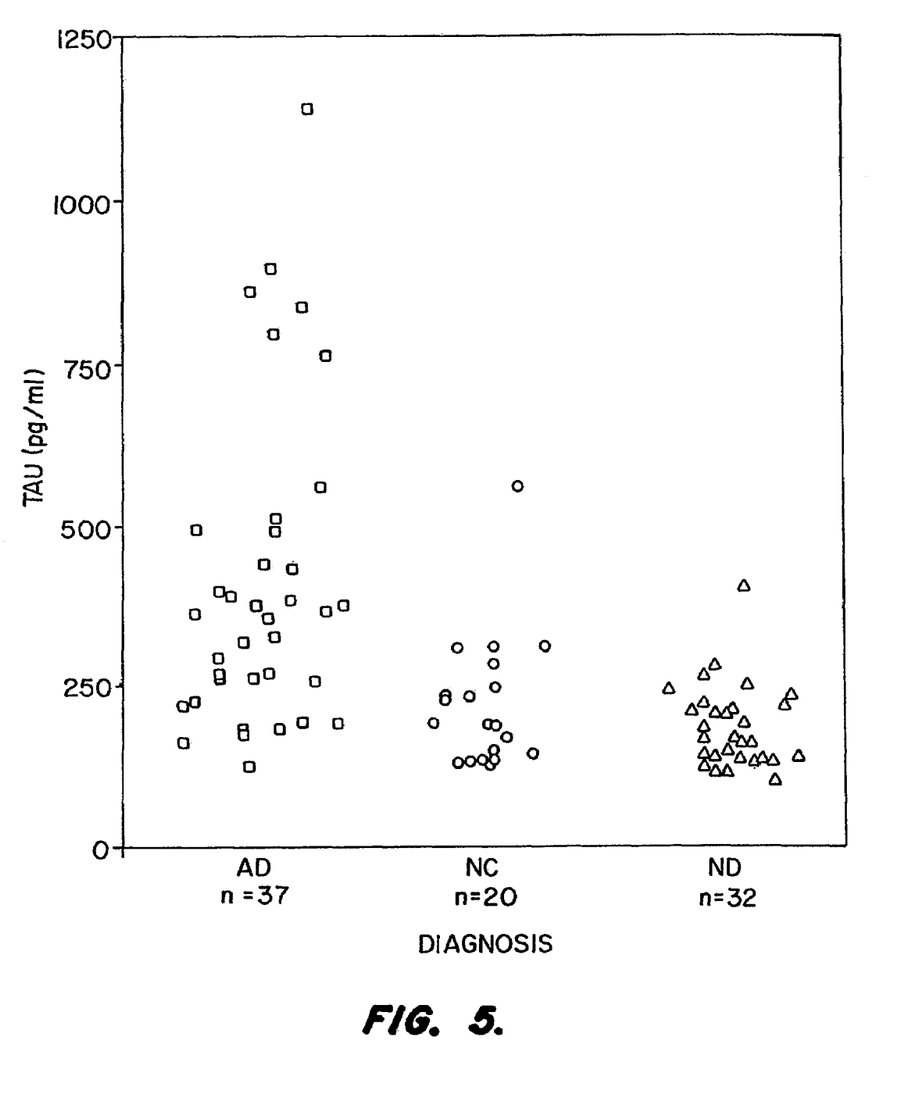
FIG. 5 shows the amounts of tau in CSF of Alzheimer's disease patients (AD), non-Alzheimer's neurological controls (ND) and non-demented control patients (NC).

Tau levels in the same subjects CSF samples were also examined. Tau measurements were performed in duplicate. To ensure consistency, several samples from previous assays were included on subsequent plates and all samples were evaluated in at least replicate measure. Replicate measures were within 15% of original values. A significant difference exists between the AD group and either control group (p<0.001). Human brain-derived tau was used as the reference standard. AD patients had a mean value of 407 pg/ml versus 168 and 212 pg/ml in neurological and normal controls, respectively (FIG. 5). This difference between the AD group and the other groups is significant at p<0.001. Employing a cutoff of 312 pg/ml, individuals with values above this level had a very high likelihood of Alzheimer's disease (22/24=92%). Only one NC and one ND subject registered above this cutoff. Separate analysis of average CSF Aβ, Aβ(x-≧41) or tau levels obtained from each center did not reveal differences between centers that were statistically significant for any of the disease categories as revealed by one-way analysis of variance. Of particular interest was the simultaneous analysis of Aβ(x-≧41) and tau measurements in the same CSF samples (FIG. 6). FIG. 6 is divided into four quadrants using the cutoffs for Aβ(x-≧41) and tau previously described. The presence of both elevated tau and reduced Aβ(x-≧41) (lower-right quadrant) was highly predictive of AD (22/23=96%). Conversely, high Aβ(x-≧41) and low tau (upper-left quadrant) was represented entirely by control patients (FIG. 6). More than half (58.7%) of all the individuals in this study fell into one of these two quadrants. The remaining patients exhibited low Aβ(x-≧41) and low tau levels (lower left quadrant).

Although the foregoing invention has been described in detail for purposes of clarity of understanding, it will be obvious that certain modifications may be practiced within the scope of the appended claims.

All publications and patent documents cited in this application are incorporated by reference in their entirety for all purposes to the same extent as if each individual publication or patent document were so individually denoted.

What is claimed is:

1. A method for screening a compound to determine its ability to alter the amount of an Aβ(x-≧41) peptide in a cerebral spinal fluid sample comprising:
   measuring a first amount of one or more soluble Aβ(x-≧41) peptides in the cerebral spinal fluid sample of a non-human animal model that expresses amyloid-β precursor protein (APP) in the brain and processes it to the one or more soluble Aβ peptides;

administering the compound to the non-human animal model;

measuring a second amount of the one or more soluble Aβ peptides in the cerebral spinal fluid sample of the non-human animal model; and comparing the first amount with the second amount, the difference indicating whether the compound increases, decreases, or leaves unchanged the amount of soluble Aβ(x-≧41) in the cerebral spinal fluid sample, wherein the amount of Aβ(x-≧41) is measured by exposing the cerebral spinal fluid to an antibody or fragment thereof specific for an epitope of Aβ(x-≧41) but that does not cross react with an epitope of Aβ(x-≦40).

2. The method of claim 1, wherein the non-human animal model is a transgenic rodent model of Alzheimer's disease.

3. The method of claim 2, wherein the transgenic rodent model is a mouse model.

4. The method of claim 1, wherein the non-human animal model is a transgenic rodent model having an expression cassette that drives the expression of a sequence which encodes the Swedish mutation of an amyloid precursor protein (APP) gene.

5. The method of claim 1, wherein the antibody or fragment thereof binds to Aβ(x-42).

6. The method of claim 1, wherein antibody or fragment thereof is an antibody recognizing an epitope on Aβ having amino acid residues 33-42.

7. The method of claim 6, wherein the antibody or fragment thereof is an antibody that will bind to Aβ(x-≧41).

8. The method of claim 6, wherein the antibody or fragment thereof is an antibody that will bind to Aβ(x-≧43).

* * * * *

```
                           SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
         (A) LENGTH: 43 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 1:

Asp Ala Glu Phe Arg His Asp Ser Gly Tyr Glu Val His His Gln Lys
1               5                  10                  15

Leu Val Phe Phe Ala Gly Asp Val Gly Ser Asn Lys Gly Ala Ile Ile
            20                  25                  30

Gly Leu Met Val Gly Gly Val Val Ile Ala Thr
        35                  40

(2) INFORMATION FOR SEQ ID NO: 2:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 2:

Gly Leu Met Val Gly Gly Val Val Ile Ala
1               5                  10
```